United States Patent
Sieber

(10) Patent No.: US 7,905,028 B2
(45) Date of Patent: Mar. 15, 2011

(54) SYSTEMS AND METHODS FOR COLLECTING BODY MEASUREMENTS, VIRTUALLY SIMULATING MODELS OF ACTUAL AND TARGET BODY SHAPES, ASCERTAINING GARMENT SIZE FITTING, AND PROCESSING GARMENT ORDERS

(75) Inventor: Stephen Sieber, Burtonsville, MD (US)

(73) Assignee: William A. Ward, Jackson, WY (US)

( * ) Notice: Subject to any disclaimer, the term of this patent is extended or adjusted under 35 U.S.C. 154(b) by 131 days.

(21) Appl. No.: 12/248,276

(22) Filed: Oct. 9, 2008

(65) Prior Publication Data

US 2009/0193675 A1    Aug. 6, 2009

Related U.S. Application Data

(60) Provisional application No. 61/025,893, filed on Feb. 4, 2008.

(51) Int. Cl.
*A61B 5/103* (2006.01)
*G01B 1/00* (2006.01)

(52) U.S. Cl. ............................................ 33/512; 33/3 C

(58) Field of Classification Search ............ 33/511–512, 33/2 R, 4–5, 3 C, 11, 14–16, 23.09, 755–756, 33/759, 555.1
See application file for complete search history.

(56) References Cited

U.S. PATENT DOCUMENTS

| | | | |
|---|---|---|---|
| 4,742 A | 9/1846 | Acton | |
| 167,957 A | 9/1875 | Ullrich | |
| 460,282 A | 9/1891 | Smith | |
| 545,139 A | 8/1895 | Start, Jr. et al. | |
| 650,389 A | 5/1900 | Hatfield | |
| 734,279 A | 7/1903 | O'Donnell et al. | |
| 740,943 A | 10/1903 | Summersby et al. | |
| 846,461 A | 3/1907 | Engel | |
| 988,683 A | 4/1911 | Wurtzel | |
| 991,103 A | 5/1911 | Titchell | |
| 1,079,333 A | 11/1913 | Goldberger | |
| 1,096,975 A | 5/1914 | Watters | |
| 1,248,035 A | 11/1917 | Taylor | |
| 1,262,376 A | 4/1918 | Moyer | |
| 1,339,896 A | 5/1920 | Kemper | |
| 1,414,481 A | 5/1922 | Moe | |
| 1,521,054 A | 12/1924 | Sniegocki | |
| 1,784,888 A | 12/1930 | Couture | |
| 2,199,530 A | 5/1940 | Thompson | |
| 2,205,626 A | 6/1940 | Mason | |
| 3,405,852 A | 10/1968 | Fox | |
| 3,685,155 A | 8/1972 | Oblander | |
| 4,149,246 A | 4/1979 | Goldman | |

(Continued)

FOREIGN PATENT DOCUMENTS

DE    10 2004 055650 A1    5/2006

*Primary Examiner* — Yaritza Guadalupe-McCall

(74) *Attorney, Agent, or Firm* — Berenato & White, LLC

(57) ABSTRACT

Methods and systems are provided for obtaining coordinated body measurements of an individual using a measuring device having a belt with a first scale of measurement indicia and a strip with a second scale of measurement indicia. Also provided are a method and system of virtually rendering a simulated model of an actual body shape and a target body shape of an individual. Methods and systems of size fitting garments and processing garment orders are also provided.

27 Claims, 23 Drawing Sheets

U.S. PATENT DOCUMENTS

| | | |
|---|---|---|
| 4,598,376 A | 7/1986 | Burton et al. |
| 4,635,367 A | 1/1987 | Vigede |
| 4,651,427 A | 3/1987 | Perry |
| 4,730,646 A | 3/1988 | Traub |
| 4,868,990 A | 9/1989 | Steinberg |
| 4,875,296 A | 10/1989 | Holzmeister et al. |
| 5,163,007 A | 11/1992 | Slitlaty |
| 5,515,268 A | 5/1996 | Yoda |
| 5,732,475 A | 3/1998 | Sacks et al. |
| 5,930,769 A | 7/1999 | Rose |
| 6,353,770 B1 | 3/2002 | Ramsey et al. |
| 6,401,350 B2 | 6/2002 | Ford |
| 6,415,199 B1 | 7/2002 | Liebermann |
| 6,546,309 B1 | 4/2003 | Gazzulolo |
| 6,640,460 B1 | 11/2003 | Nabarro et al. |
| 6,711,455 B1 | 3/2004 | Holloway et al. |
| 6,891,381 B2 | 5/2005 | Bailey et al. |
| D507,392 S | 7/2005 | Sieber |
| 6,931,747 B2 * | 8/2005 | Rego ............................... 33/512 |
| 7,020,538 B2 | 3/2006 | Luhnow |
| 7,114,260 B2 | 10/2006 | Nguyen |
| D533,094 S | 12/2006 | Sieber |
| 7,146,239 B2 | 12/2006 | Feld et al. |
| 7,149,665 B2 | 12/2006 | Feld et al. |
| 7,164,962 B2 | 1/2007 | Petterson |
| 7,239,151 B2 | 7/2007 | Bailey et al. |
| 7,249,423 B2 | 7/2007 | Sieber |
| 7,260,445 B2 | 8/2007 | Weiser et al. |
| D581,300 S | 11/2008 | Sieber |
| 7,685,727 B2 | 3/2010 | Sieber |
| 2002/0166254 A1 | 11/2002 | Liebermann |
| 2003/0076318 A1 | 4/2003 | Shaw-Weeks |
| 2004/0049435 A1 | 3/2004 | Nabarro |
| 2005/0034317 A1 | 2/2005 | Burandt et al. |
| 2006/0190122 A1 | 8/2006 | Loeb |
| 2006/0195219 A1 | 8/2006 | Luhnow et al. |
| 2006/0265892 A1 | 11/2006 | Sieber |
| 2008/0184575 A1 | 8/2008 | Sieber |

* cited by examiner

Ankle 35

Calk 54

Thigh 82

Buttocks 148

Waist 99

Chest 136

Head 87

Neck 49

Bicep 43

Forearm 37

Wrist 26

Waistband 133

Rise 74

Pant Length 151

SYSTEMS AND METHODS FOR COLLECTING BODY MEASUREMENTS, VIRTUALLY SIMULATING MODELS OF ACTUAL AND TARGET BODY SHAPES, ASCERTAINING GARMENT SIZE FITTING, AND PROCESSING GARMENT ORDERS

CROSS-REFERENCE TO RELATED APPLICATION(S)

This application claims the benefit of priority under 35 U.S.C. §119(e) of provisional patent application 61/025,893 filed Feb. 4, 2008, the complete disclosure of which is incorporated herein by reference.

FIELD OF THE INVENTION

The present invention relates to systems and methods for measuring and recording body measurements of an individual for, among other things, body imaging and health and fitness tracking. The present invention also relates to systems and methods of simulating virtual models rendered to depict the appearance of an individual based on actual body measurements of the individual and target body measurements which are the goal of the individual. The present invention further relates to systems and methods of providing shoppers, including online shoppers, with automated, individualized size fitting selection of garments (wearable articles). The present invention still further relates to systems and methods for processing garment orders, especially online garment orders. The present invention still further relates to measurement devices.

BACKGROUND OF THE INVENTION

Consumers commit a large amount of their disposable income and available time to improving or maintaining their health and appearance through proper exercise and diet. It has been reported by the National Sporting Goods Association that Americans alone spend billions of dollars annually on sporting and exercise equipment. See NSGA Analysis: Sporting Goods Store Sales in New England Grew 22.5% from 1997 to 2002; Sporting Goods Sales Reach $52.1 Billion in 2006; NSGA Expects 3% Growth in 2007. Health club memberships among Americans number in the tens of millions. See The American Fitness Industry's Plan for Growth: 50 Million Members by 2010. Americans spend billions of dollars annually on diet plans and products AARP.

Difficulties often arise in tracking the progress that an individual achieves through exercise and diet. Perhaps the most common barometer for determining progress is weight loss. Many people correlate the successfulness of a diet and weight loss program proportionally to their overall weight loss. However, many exercise programs today encourage muscular development in conjunction with fat loss for achieving better fitness and longevity. Straight calculations of weight loss do not factor in muscle weight gains. Conventional scales only indicate total weight change of the entire body, and do not account for the composition of that weight, i.e., how much is fat and how much is muscle. Thus, for example, a person who sheds 10 pounds of fat while gaining 2 pounds of muscle will only decipher from a conventional scale the loss of 8 pounds overall. The building of desirable muscle mass can distort the perceived effectiveness of a dieting and exercise program evaluated solely on the basis of weight loss.

Another problem associated with using weight loss as the primary benchmark for setting exercise and diet routine goals is that the individual, while having an ideal body shape and appearance pictured in their head, will not always be able to predict accurately what target weight loss is required to attain their ideal body shape and appearance. The individual may reach a target weight loss through their exercise and diet routine only to find, for example, that their target weight was not realistically low enough to allow them to fit into a particular size dress.

Another touchstone by which exercise and dieting programs are evaluated involves the periodic measurement of body part circumferences by the individual over the course of the program. An individual may measure and record the circumference of their buttocks or waist at the beginning of a program, and thereafter make additional periodic measurements over the course of the program, such as on a weekly basis, to track and evaluate progress. Successful completion of an exercise and dieting program or a phase thereof is signified when the individual reaches a target or goal body circumferential measurement.

The use of body measurements for evaluating a program's effectiveness is not without its problems. For one, the accuracy of this procedure depends greatly on measurement repeatability. The measuring device must be placed at an identical location on the body part each time the measurement is repeated. Because body parts possess curvatures and taper, if a measurement device is placed on an individual's body part, such as a thigh, at a location higher or lower than the placement for a previous periodic measurement of the same body part, the difference in recorded measurements may not reflect an accurate and precise comparison for reliably evaluating progress over the dieting and exercise period.

Still another problem of tracking progress by body measurement is that individuals usually fixate on a single body part and focus their attention only on that body part. Although fat loss occurs generally proportionally throughout the body as weight is lost, for certain individuals fat deposited, for example, at the thighs and waist often may be the "last to go." See Scientific Psychic, Weight Control. Hence, an individual may become frustrated because, for example, diminutive waistline losses might not fully reflect greater overall weight loss more pronounced in other body areas, such as the thighs. Additionally, individuals are often not able to predict quantitatively what body part measurements are required in order to reach their desired body appearance and shape. Consequently, the individual may set a target goal body part measurement that is either insufficient or excessive for attaining an ideal body shape and image desired by the individual. Hence, accurate and repeatable body measurement routines are extremely valuable for tracking health and fitness progress and evaluating the effectiveness of an exercise or dieting program.

Additionally, the accurate and repeatable measurement routines can provide advantages to individuals in their selection and purchase of properly fitting garments.

Traditionally, consumers made a majority of their clothing and fitness garments purchases at retail outlets, such as department stores and specialty stores. Commonly, the consumer travels to one or more stores and visually inspects the stores' merchandise to select those products that meet his or her preferences. The retailer typically furnishes changing rooms and mirrors on their premises so that the consumer may try on and model the clothing so as to assess the fit and appearance of the clothing before making a purchasing decision. The retailer may also offer in-store consultants for providing advice on appearance and fit, and tailors for making custom alterations. One advantage of traditional in-store retail sales has been the opportunity for the consumer to try on multiple size garments and select which size fits best. Although the process is time consuming, it saves the consumer the inconvenience of returning garments which, when tried on at home for the first time, do not properly fit.

Most garments are made available to consumers for purchase in ready-to-wear stock sizes. Consumers typically estimate their garment size, and then proceed through a trial-and-error process of trying on garments of different sizes close to their estimated size until arriving at a size that fits best. This trial-and-error process permits "normal size" consumers to obtain garments that overall fit well enough to wear comfortably and fashionably. Depending upon eccentricities in the body of the consumer, however, for many consumers a garment may properly fit one body part while improperly fitting another body part. For example, traditional dress shirts such as used for men's business attire are often available by neck size and arm length. However, discrepancies in shoulder broadness and girth, even between individuals sharing common neck sizes and sleeve lengths, can result in the shirt properly fitting one individual and improperly fitting another individual of different girth.

Proper fitting of currently available stock sized garments often presents additional problems. Although most manufacturers adopt standard numbered sizes or more indefinite designations such as small, medium, large, etc., there can be wide discrepancies in the actual measurements of a garment produced by one manufacturer when compared to that of another due to lack of size uniformity throughout the industry. As a result, consumers frequently find that although a certain size of garment produced by one manufacturer fits them, the same size garments made from another manufacturer does not fit.

Manufacturers have contributed to this problem by frequently introducing under a single label or brand different lines of clothing aimed at different classes of shoppers, such as younger individuals versus older individuals or those of smaller or larger stature as compared to those of so-called normal stature. Although manufacturers retain traditional size designations such as medium, etc. for each clothing line, the garments so designated from one line are dimensioned and fit differently than those from another line. Manufacturers routinely offer little or no guidance to the consumer as to these differences other than occasional use of somewhat vague terms such as sport, athletic, junior or petite to indicate sizing trends of the product line. It is not uncommon, therefore, for consumers to be somewhat perplexed or exasperated as they find that a garment from a particular manufacturer that bears "their" size does not fit actually them, only then to be told by a salesperson that despite the common size designations of the garments, the non-fitting garment is from a particular line of that manufacturer that runs bigger or smaller.

With the advent and proliferation of the Internet (i.e., the World Wide Web), many manufacturers, wholesalers, and retailers have diversified their sales approach by selling "online." The consumer uses his or her online connection and web browser to view the product line of a particular retail store or garment manufacturer, and to purchase a garment or garments over the Internet. Some websites assist the consumer in visualizing the fit and appearance of a particular garment by providing a digital photograph of a model wearing the garment. Alternatively, the consumer may view the garments in mail order catalogues before placing their orders online.

Online sales provide the consumer with several benefits over traditional in-store shopping. The online consumer is able to access clothing not offered by retailers within the consumer's geographical proximity. For example, online shopping permits the consumer to make international purchases of garments that otherwise might not be imported into the consumer's country or state. Another benefit of online shopping is efficiency. The consumer may scan various brands and styles online without physically traveling to a retailer store or searching through shelves of clothing for a correct style and size. Further, the in-store consumer is restricted to perusing and purchasing from the limited stock of a retail store. Sales are often thwarted because a garment desired by the consumer is not available in stock in the consumer's size. In contrast, online purchases are typically shipped from warehouses having larger stocking capacities than brick and mortar retail stores. With the exception of special orders, online orders generally ship the same or next day the order is placed and payment is made. The consumer is not the only one to benefit from online sales. An online garment retailer benefits from online sales by reaching a wider audience of potential customers than would otherwise be available due to the geographical constraints and other drawbacks of the traditional approach.

One of the more rigorous and deleterious problems experienced by online sellers resides in the transaction costs of consumer returns. Perhaps the most prominent reason for consumer returns stems from improper fit. Many objective and subjective considerations play into whether a garment fits properly, including perceived tightness, length, and comfort. Unlike the traditional approach, in which the consumer is able to physically try on multiple sizes of garments in a brick-and-mortar store for fit evaluation, online sales largely rely on the consumer's estimation of size choice based on perceptions that the consumer has over his or her own body and expectations concerning actual garment sizes. For example, the consumer may predict the appropriate size fit of a garment purchase by referring to clothing sizes in their existing wardrobes. However, consumers often have misperceptions of their own body shape and dimensions when ordering cloths. Further, as discussed above there are generally differences in garment cuts between brands, leading to a lack of a consensus among manufacturers in sizing garments. This lack of consensus is due, at least in part, to so-called vanity selling. Some companies conclude that if they put, for example, a size 4 on a label, even though the garment is closer to a true size 6, the consumer will be more likely to purchase the garment labeled with the smaller size. Furthermore, consumers often experience weight changes and growth spurts, particularly in the case of younger consumers, that cause the consumer to change sizes between purchases.

Consequently, the consumer will not get a true indication of the fit of the garment until the purchased garment has been received and tried on, usually at home, by the consumer. In instances in which the fit is not to the consumer's satisfaction, the consumer repackages the garment and ships it back to the online seller for either a refund or exchange. Returns and exchanges of online product sales cost the clothing industry millions of dollars annually. Contributing to diminished profits of online sales are shipping costs, restocking expenses, damage to returned garments, and overall dissatisfaction cost that could impact the continuing success of the brand in general.

Another problem arising from Internet ordering of standard stock-sized garments is that many Internet shoppers are only willing to consider purchasing garments over the Internet from manufacturers or manufacturers' product lines that they already own, neglecting to consider either other manufacturers or product lines. This consumer behavior presupposes that a given manufacturer does not change the cut or sizing of its garments in general or of a particular product line, which frequently is not the case.

The verbiage and charts frequently offered on web sites to help a consumer determine the appropriate size to purchase often have no positive effect. Consumers lacking tailoring experience and tools usually do not bother to go through the steps of taking complete and accurate measurements before they make a purchase of clothing, or they are confused or daunted by the task of deciphering the directions to determine their size.

At a minimum, these problems associated with Internet clothing shopping can result in increased frustration and wasted time and expense as a consumer has to send purchases back one or more times to the vendor in favor of a different size until this trial and error process hopefully results in an appropriately fitting garment. This process may lead a frustrated consumer, who might have been a loyal customer of a given brand, to either no longer shop for clothing via the Internet or no longer continue purchasing a particular manufacturer's garments.

Current fashion trends further exacerbate the problems associated with so-called stock-size garment purchases. The look, style and fit trends of clothing are ever changing. Fashion trends have caused clothing styles to run the gamut from extremely oversized garments to virtually skin-tight form-fitting garments. Some fashion trends might dictate a tight fit in one area of a garment and a loose fit in another. These fashion trends have made sizing designations further unreliable. For example, a consumer may desire high or low rise for a pair of pants or jeans to accomplish a given style or look. This can cause the waistband of the garment, for example, to ride across or very low on the hips in one instance and above or very high on the hips in another instance. Similarly, the shopper of such garments may desire the crotch of the garment to very closely follow the contour of the body or provide a considerable space of up to several inches between the wearer's crotch and the location of the crotch on the garment. These trends have rendered many traditional garment measurements, such as the inseam measurements, relatively useless because these measurements depend upon the height or location of the waistband on the wearer and the location of the rise. Traditional inseam measurements virtually never represent a standard measurement that is of any use in crafting such varied custom fashion clothing. To a lesser extent, the reliability of crotch, outer seam and length measurements has also been lessened by these trends because the measurements depend completely upon the desired location of the waistband in relation to the wearer's hips.

The search for the right stock size can be exhausting and frustrating, and often in vain because an acceptable stock size fit simply might not exist for a certain end user. In order to overcome the problems associated with stock-sized garments, consumers who are more discerning about their clothing and clothing fit or have unusual requirements in this regard have at times rejected stock-sized garments in favor of custom-made garments. A major benefit of custom-made garments is the ability to have them tailored to complement the particular body size and shape of the individual. However, custom garments are typically much more expensive than standard or ready-to-wear garments and usually require an extended time period for production of the garment. The extra expense of custom garments stems in part from the fact that production of such garments requires the time and expertise of a skilled tailor, working with a tape measure, to accurately measure the person for whom the garment is being customized. In addition to the expense, a consumer who chooses the custom garment resigns himself to the fact that he or she can not accomplish the process himself from home via the Internet and will need to make one or more trips to a tailor to complete the measuring process alone. In return for the additional time and expense invested for the custom-made garment, the consumer commonly expects precise fit and pleasing comfort in the tailored clothing. It is, therefore, imperative that the tailor have adequate tools to take precise measurements and to fit the consumer with a garment that meets the consumer's expectations.

Generally, a tailor begins a custom tailoring process by measuring his or her customer to determine various body dimensions for use in production of the custom garment. Typically, this measurement process is performed with a standard measuring tape, which the tailor applies along and around various body parts of the individual. Tailors usually work from certain "standard measurements" such as chest, waist, hip and inseam measurements. These so-called standard measurements, however, are rendered meaningless if the wearer intends to wear the clothing in a non-traditional manner, for example, if the wearer intends to locate the waistband of the finished garment at a point other than where the tailor has taken his traditional waist measurement. Errors in judgment of waistband location by the tailor or consumer during the measurement process are reflected in the fit of the tailored garment when the consumer tries on the pants but places the waistband at a different height than originally estimated using the tape measure. Such judgment errors, whether attributable to the consumer or tailor, cause the tailor to bear the additional time and expense of altering the garment or may even require the garment to be remade. Alteration and start-over delays serve to increase expense and consumer frustration.

A further problem associated with tailoring using a conventional measuring tape is that the tailoring process involves taking multiple measurements that are interrelated with one another. For example, when measuring for the waistband for a pair of pants, the height on the customer's waist at which the measuring tape is placed will directly affect pants length and crotch measurements, which typically start at the waistband. It is therefore important that pants leg measurement start from the same location where the waistband measurement was taken and not from some standard waist measurement location not coinciding to the actual waistband level.

SUMMARY OF THE INVENTION

According to a first aspect of the invention, a method is provided for obtaining coordinated body measurements of an individual. The method is performed with a measurement device featuring a belt and a strap. The belt includes a flexible belt body having a belt face with a first scale of first measurement indicia. The strap is attached to the belt, and includes a flexible strap body having a strap face with a second scale of second measurement indicia for measuring distance from a first reference point on the belt. The belt is encircled around a body part of an individual for whom body measurements are to be taken, and a first circumferential measurement is registered from the first scale. While retaining the belt encircled around the body part at a location that the first circumferential measurement is registered, a length measurement from the first reference point to an established second reference point is registered from the second scale. The measurement device is removed from the body part. For subsequent measurements of the body part, the second scale of the strip is used as a calibration tool for positioning the first reference point on the belt apart from the established second reference point by a distance equal to the length measurement so as to position the belt at the location that the first circumferential measurement was registered. A second circumferential measurement is registered from the first scale with the belt encircled around the body part at the same location on the body part that the first circumferential measurement was registered.

A second aspect of the invention provides a system for obtaining coordinated body measurements of an individual. The system includes instructions to obtain the body measurements with a measurement device featuring a belt and an attached strap. The belt includes a flexible belt body having a belt face with a first scale of first measurement indicia. The strap includes a flexible strap body having a strap face with a second scale of second measurement indicia for measuring distance from a first reference point on the belt. The instructions include encircling a belt of a measurement device around a body part of an individual for whom body measurements are to be taken; registering a first circumferential measurement from the first scale; while retaining the belt encircled around the body part at a location that the first circumferential measurement is registered, registering from the second scale a length measurement from the first reference point to an established second reference point; after removing the measurement device from the body part, again encircling the belt around the body part of the individual; calibrating with the second scale to position the first reference point on the belt apart from the established second reference point by a distance equal to the length measurement so as to position the belt at the location that the first circumferential measurement was registered; and registering a second circumferential measurement from the first scale with the belt positioned at the same location on the body part that the first circumferential measurement was registered.

According to a third aspect of the invention a method is provided for obtaining coordinated body measurements of an individual. The method is carried out with a measurement device featuring a belt and a strap attached to the belt. The belt includes a flexible belt body having a belt face with a first scale of first measurement indicia. The strap includes a flexible strap body having a strap face with a second scale of second measurement indicia for measuring distance from a first reference point on the belt. According to the method, the belt is encircled around a first body part of an individual for whom body measurements are to be taken, and a first circumferential measurement is registered from the first scale. While retaining the belt encircled around the first body part at a location that the first circumferential measurement is registered, a first length measurement to a common second reference point is registered with the second scale. The belt is encircled around a second body part of the individual, and a second circumferential measurement is registered from the first scale. While retaining the belt encircled around the second body part at a location that the second circumferential measurement is registered, a second length measurement to the common second reference point is registered with the second scale.

A fourth aspect of the invention provides a system for obtaining coordinated body measurements of an individual using a measurement device featuring a belt and a strap. The belt includes a flexible belt body having a belt face with a first scale of first measurement indicia. The strap is attached to the belt, and includes a flexible strap body having a strap face with a second scale of second measurement indicia for measuring distance from a first reference point on the belt. The instructions include encircling the belt around a first body part of an individual for whom body measurements are to be taken; registering a first circumferential measurement from the first scale; while retaining the belt encircled around the first body part at a location that the first circumferential measurement is registered, registering with the second scale a first length measurement to a common second reference point; encircling the belt around a second body part of the individual, the second body part differing from the first body part; registering a second circumferential measurement from the first scale; and while retaining the belt encircled around the second body part at a location that the second circumferential measurement is registered, registering with the second scale a second length measurement to the common second reference point.

A fifth aspect of the invention provides a method of virtually rendering a simulated model of an individual's actual body shape and an individual's target body shape through the use of virtual imaging. According to the method, actual body measurement data of an individual are received, and a first virtual model rendered to depict the appearance of the individual based on the actual body measurement data is displayed. The target body measurement data of the individual are also received, and a second virtual model rendered to depict a target appearance of the individual based on the target body measurement data is displayed.

A sixth aspect of the invention provides a system for virtually rendering a simulated model of an individual's actual body shape and a user target body shape for determining goal body measurements through the use of virtual imaging. The system features an input device, a programmed device, and a display device. The input device permits entry of actual body measurement data of an individual and entry of target body measurement data of the individual. The programmed device receives the actual body measurement data of the individual and generates a first virtual model rendered to depict the appearance of the individual based on the actual body measurement data, and receives the target body measurement data of the individual and generates a second virtual model rendered to depict a target appearance of the individual based on the target body measurement data. The first and second virtual models are viewable from the display device.

According to a seventh aspect of the invention, a method of size fitting garments is provided. The method features storing personal contact information and body measurements of multiple garment end users in a first database, and storing garment pattern specifications of multiple garment items offered by a garment product provider in a second database. The garment pattern specifications are ascertained from actual measurements of patterns of standard fit sizes of the garment items. The body measurements are obtained with a measurement device including a belt having a first scale of first measurement indicia, and a strap attached to the belt having a second scale of second measurement indicia. A first body measurement is obtained from the belt placed at a first position on an individual garment end user and a second measurement is obtained from the strap while the belt is maintained at the first position. An order for a garment item selected from the multiple garment items is received from a garment shopper, as is the personal contact information of an individual garment end user of the multiple garment end users for whom the selected garment item is to be purchased. The body measurements of the individual garment end user are compared to the pattern specifications of the standard fit sizes of the selected garment item. Based on the comparison a selected standard fit size of the garment is automatically selected for the garment shopper.

An eighth aspect of the invention provides a method of processing online retail garment orders. The method features storing personal contact information and body measurements of multiple garment end users in a first database of an online retailer, and storing garment pattern specifications of patterns of multiple garment items offered by a garment product provider in a second database of the online retailer. The garment pattern specifications include actual measurements of standard fit sizes of the garment items. An order for a garment item selected from the multiple garment items, and the personal contact information of an individual garment end user of the multiple garment end users for whom the selected garment item is to be purchased, are received by the online retailer from a garment shopper. The body measurements of the individual garment end user are compared to the pattern specifications of the standard fit sizes of the selected garment item, and an appropriate standard fit size of the selected garment item is automatically selected based on the comparison by the online retailer. The online retailer collects payment from the garment shopper, and a portion of the payment is transmitted to the garment product provider of the selected garment item. The order is processed for delivery to the shopper or end user or other shipping address.

According to a ninth aspect of the invention, a system featuring software and hardware is provided for implementing a method of size fitting garments. The system is configured to: store personal contact information and body measurements of multiple garment end users in a first database, the body measurements being obtained with a measurement device including a belt having a first scale of first measurement indicia and a strap having a second scale of second measurement indicia, the strap being attached to the belt, whereby a first body measurement is obtained from the belt placed at a first position on an individual garment end user and a second measurement is obtained from the strap while the belt is maintained at the first position; store garment pattern specifications of multiple garment items offered by a garment product provider in a second database, the garment pattern specifications ascertained from actual measurements of patterns of standard fit sizes of the garment items; receive from a garment shopper an order for a garment item selected from the multiple garment items and the personal contact information of an individual garment end user of the multiple garment end users for whom the selected garment item is to be purchased; compare the body measurements of the individual garment end user, including at least the first body measurement, to the pattern specifications of the standard fit sizes of the selected garment item; and automatically select for the garment shopper an appropriate standard fit size of the selected garment based on the comparison.

A tenth aspect of the invention provides a system featuring software and hardware for implementing a method of processing online retail garment orders. The system is configured to allow the online retailer to: store personal contact information and body measurements of multiple garment end users in a first database of the online retailer; store garment pattern specifications of multiple garment items offered by a garment product provider in a second database of the online retailer, the garment pattern specifications ascertained from actual measurements of patterns of standard fit sizes of the garment items; receive from a garment shopper an order for a garment item selected from the multiple garment items and the personal contact information of an individual garment end user of the multiple garment end users for whom the selected garment item is to be purchased; compare the body measurements of the individual garment end user to the pattern specifications of the standard fit sizes of the selected garment item; automatically selected for the garment shopper one of the standard fit sizes of the selected garment item based on the comparison; collect payment from the garment shopper and transmit a portion of the payment to the garment product provider of the selected garment item; and process the order for shipment.

An eleventh aspect of the invention provides a measurement device featuring a belt including a flexible belt body capable of being encircled about a body part of an individual, the belt body having first and second ends and opposite first and second belt faces. The first belt face has a scale of measurement indicia for providing at least one of length and circumference measurements. The first end of the belt includes a bracket with an aperture through which the belt passes. The second end includes a locking member having a size that is larger than the aperture such that the second end cannot pass through the aperture, whereby said belt is formed as a closed loop.

A twelfth aspect of the invention provides a method of taking body measurements with the measurement device of the eleventh aspect. The method features measuring a body part with a body measurement device including a belt. The belt has a flexible belt body capable of being encircled about a body part of an individual. The belt body has first and second ends and opposite first and second belt faces. The first belt face has a scale of measurement indicia for providing at least one of length and circumference measurements. The first end of the belt includes a bracket with an aperture through which the belt passes. The second end includes a locking member having a size that is larger than the aperture such that the second end cannot pass through the aperture, whereby said belt is formed as a closed loop.

Additional aspects of the invention will become apparent upon viewing the accompanying drawings and reading the following detailed description of the invention.

BRIEF DESCRIPTION OF THE DRAWINGS

The accompanying drawings are incorporated in and constitute a part of the specification. The drawings, together with the general description given above and the detailed description of the exemplary embodiments and methods given below, serve to explain the principles of the invention. In such drawings.

Figure 1:
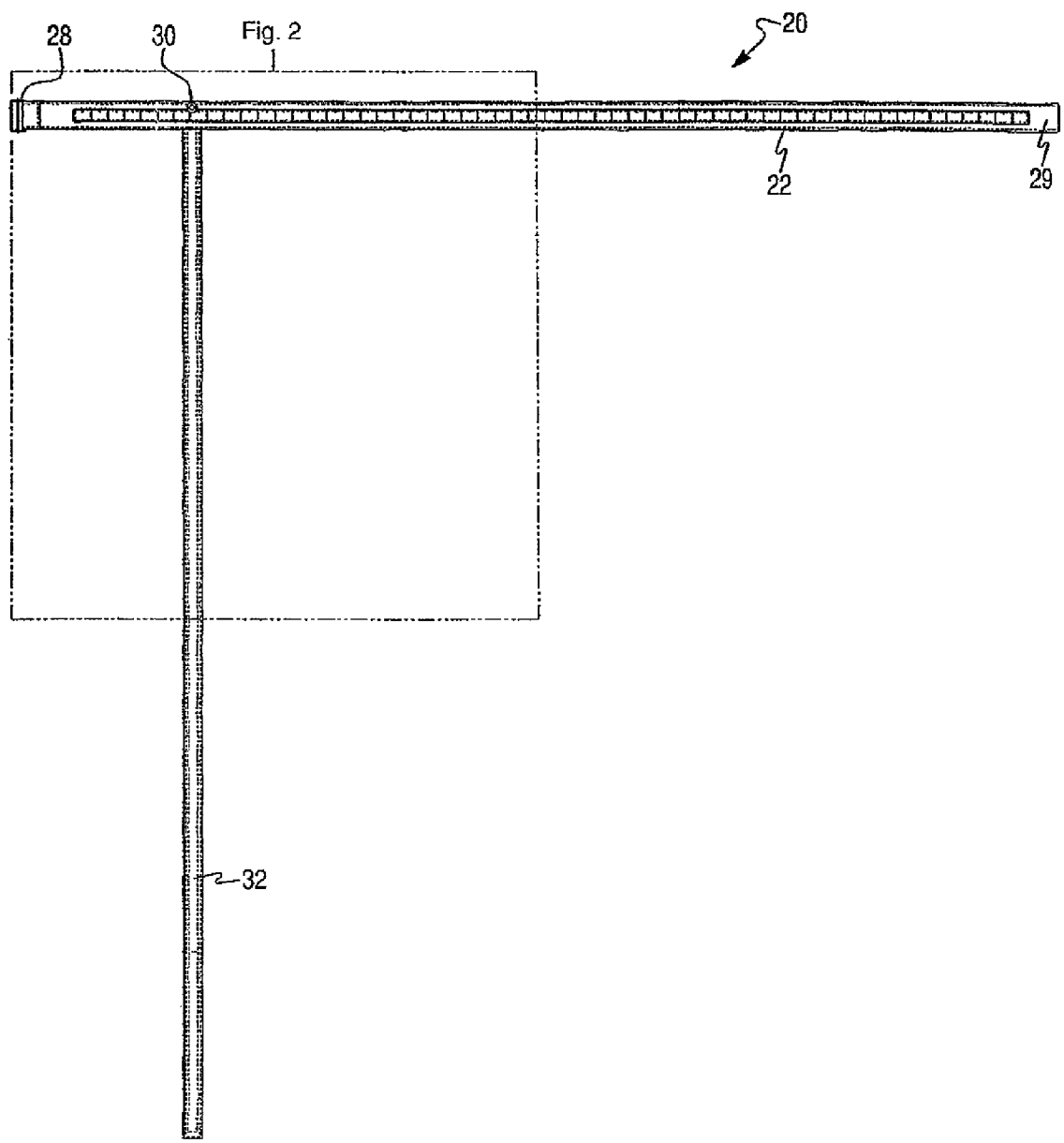
FIG. 1 is a top view of a measuring device according to an embodiment of the invention.

DETAILED DESCRIPTION OF EXEMPLARY EMBODIMENTS AND EXEMPLARY METHODS OF THE INVENTION

Reference will now be made in detail to the presently exemplified embodiments and methods of the invention as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the exemplary embodiments and methods. The invention according to its various aspects is particularly pointed out and distinctly claimed in the attached claims read in view of this specification, and appropriate equivalents.

A first embodiment for obtaining coordinated body measurements of an individual is described below with reference to the accompanying drawings, especially FIGS. 20-34. The embodiment may be implemented as a system and method, and is particularly useful for tracking changes to an individual's body shape over a period of time, such as a time period corresponding to a dieting and/or exercise program. Health clubs and dieting centers may incorporate the embodiment into their programs to track an individual's progress towards attaining a desired body shape. This embodiment may be implemented online to allow individuals to access and enter personal body measurements from remote locations, such as the comfort of their home, rather than traveling to the health club or dieting center.

This embodiment is carried out with a measurement device. Exemplary measurement devices are described in greater detail below, the description of which is incorporated by reference into this embodiment. Generally, an exemplary measurement device includes a belt and a strap. The belt includes a flexible belt body having a belt face with a first scale of first measurement indicia. The strap is attached to the belt, and includes a flexible strap body having a strap face has a second scale of second measurement indicia for measuring distance from a first reference point on the belt. The first and second measurement indicia may be the same or different from one another, e.g., both may be inches, or one may be centimeters and the other millimeters.

Figure 21:
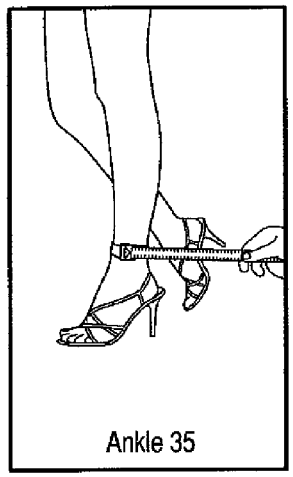
FIG. 21 is a photograph showing a measuring device applied to an individual for taking an ankle body measurement.
Figure 22:
FIG. 22 is a photograph showing a measuring device applied to an individual for taking a calf body measurement.

In order to obtain coordinated body measurements of an individual according to an embodiment of the invention, the belt is encircled around a body part of an individual for whom body measurements are to be taken, and a first circumferential measurement is registered from the first scale. FIGS. 21-24 respectively depict the belt encircled around an ankle, calf, thigh, and buttocks of an individual for registering respective body measurements. While retaining the belt encircled around the body part, the second scale is used to measure a length measurement to an established or common second reference point. In an exemplary embodiment the second reference point is the ground or other surface on which the individual is standing while taking the measurement. For instance, to measure an ankle of the individual as shown in FIG. 21, the circumference around the ankle is measured by the first scale of the belt. The vertical location of the first reference point, and hence the position of the belt when the circumferential measurement is made, is then taken in reference to the second reference point, such as the ground. The distance between the first and second reference points is registered as a length measurement using the second scale. The same procedure may be repeated with respect to other body parts, such as the calf, thigh, and buttocks, each having its circumference measured in reference to a distance to a common reference point, e.g., the ground.

Figure 23:
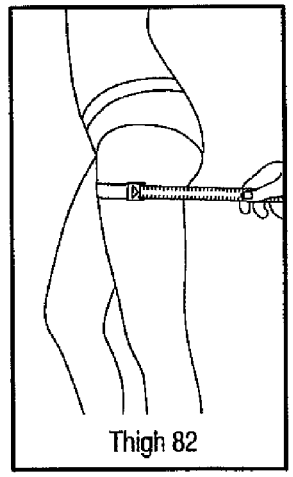
FIG. 23 is a photograph showing a measuring device applied to an individual for taking a thigh body measurement.
Figure 24:
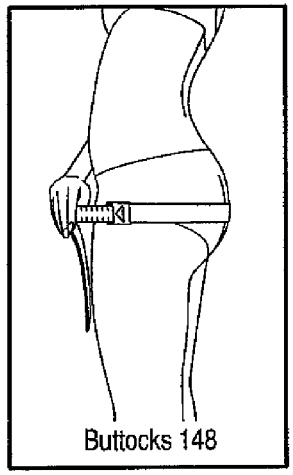
FIG. 24 is a photograph showing a measuring device applied to an individual for taking a buttocks body measurement.
Figure 25:
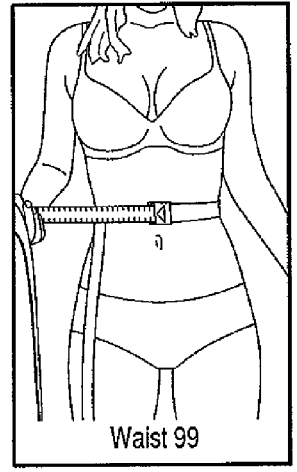
FIG. 25 is a photograph showing a measuring device applied to an individual for taking a waist body measurement.
Figure 26:
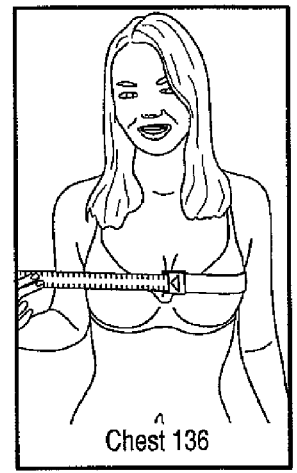
FIG. 26 is a photograph showing a measuring device applied to an individual for taking a chest body measurement.
Figure 27:
FIG. 27 is a photograph showing a measuring device applied to an individual for taking a head body measurement.
Figure 28:
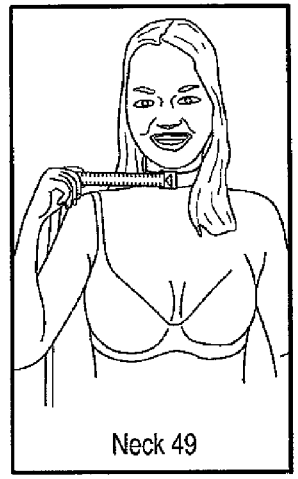
FIG. 28 is a photograph showing a measuring device applied to an individual for taking a neck body measurement.

The established nature of the second reference point provides a fixed coordinate from which subsequent measurements may be made to improve the accuracy of repeat measurements, i.e., ensuring that all circumferential measurements for a given body part are made at the same height or location on the body part. For example, an individual's thigh generally tapers from the buttocks to the knee, as shown in FIG. 23. The measured value of the thigh's circumference will depend upon the height on the thigh at which the belt is positioned for registering the circumferential measurement. To provide meaningful tracking of thigh measurements taken over a period of time, it is important that the belt be repeatedly located at an identical position on the thigh for each measurement to negate any influence that the natural tapering of the thigh might otherwise have on the measurements. After a period of time has passed in which the individual has exercised or dieted, such as weekly or monthly, the belt is again encircled around the body part of the individual to take a second circumferential measurement. To ensure that the first and second circumferential measurements are taken at the same location along the thigh, the second scale is used to calibrate the position of the belt. The first reference point on the belt is set apart from the second reference point (e.g., the ground) by a distance equal to the length measurement taken at the time the first circumferential measurement was registered, and the second circumferential measurement is registered. Employing the strip as a calibrating device allows the belt to be repeatedly positioned at the same location on the body for registering circumferential measurements. This procedure may be repeated using respective length measurements for each body part.

The second reference point also is beneficial in providing a common reference from which each of the circumferential measurements may be referenced relative to one another. The coordinating of body part circumferential measurements is also referred to herein as body mapping, and facilitates rendering of a simulated model of the body shape of the individual.

FIGS. 25-28 illustrate the use of a measurement device for measuring the circumference of the waist, chest, head, and neck, respectively. For each measurement, a common second reference point is taken. The curvature of the hips and buttocks may obstruct the strap from extending along a straight vertical path between the circumferential measuring point on the measured body part and the ground. Consequently, the ground might not be an effective second reference point for obtaining accurate and repeatable calibrating measurements. Accordingly, an alternative reference point may be selected. The alternative reference point may be, for example, the waist, buttocks, belly button, or birthmark, among other points.

Figure 29:
FIG. 29 is a photograph showing a measuring device applied to an individual for taking a bicep body measurement.
Figure 30:
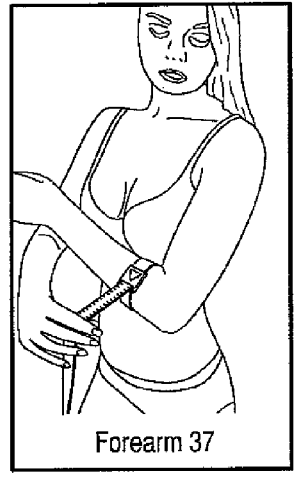
FIG. 30 is a photograph showing a measuring device applied to an individual for taking a forearm body measurement.
Figure 31:
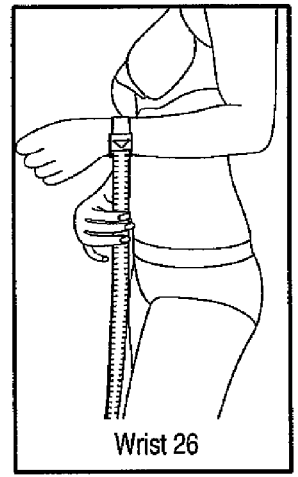
FIG. 31 is a photograph showing a measuring device applied to an individual for taking a wrist ankle body measurement.
Figure 32:
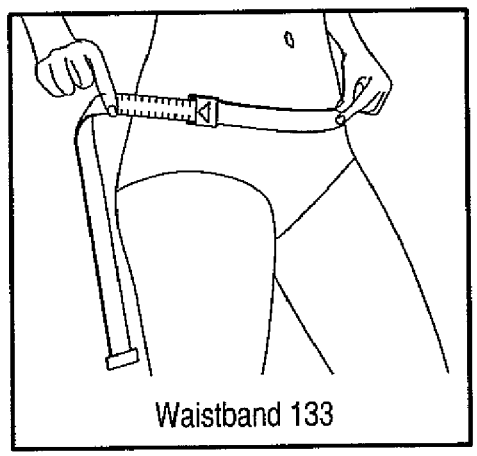
FIG. 32 is a photograph showing a measuring device applied to an individual for taking a waistband body measurement.
Figure 33:
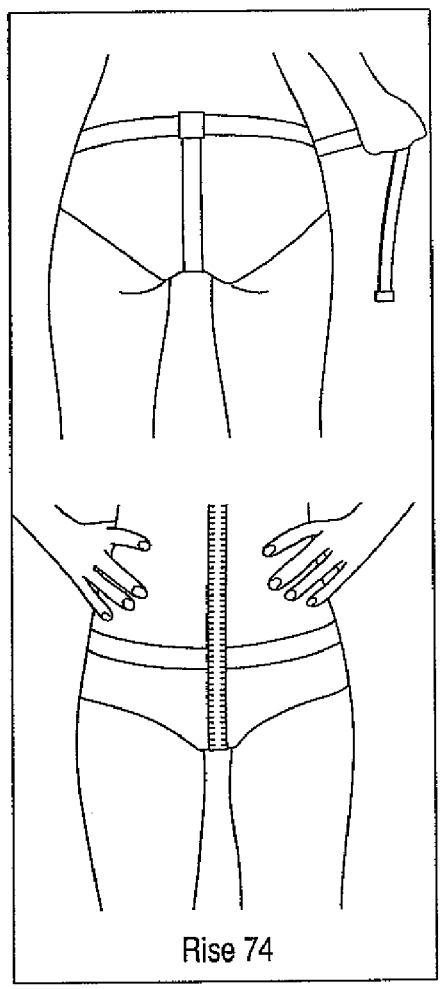
FIG. 33 is a photograph showing a measuring device applied to an individual for taking a rise body measurement.
Figure 34:
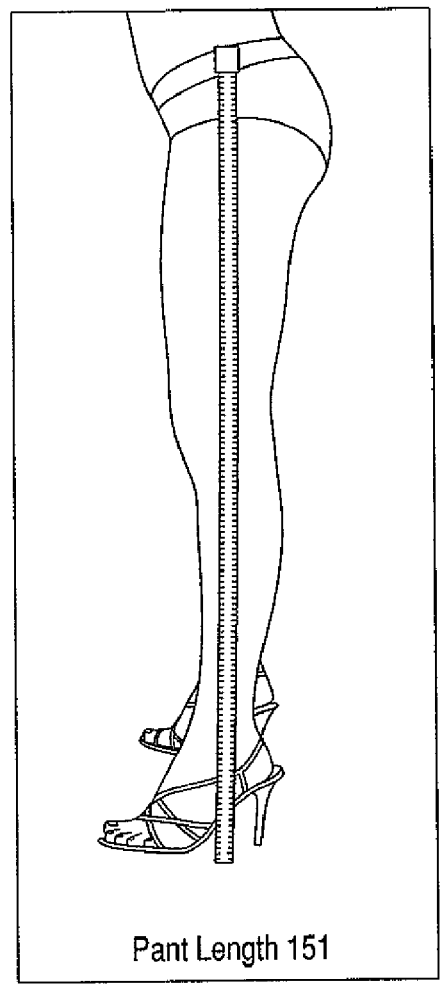
FIG. 34 is a photograph showing a measuring device applied to an individual for taking a pant length measurement.

FIGS. 29-31 illustrate an implementation in which the measurement device is encircled about upper extremities for registering circumferential body measurements of the bicep, forearm, and wrist, respectively. A common reference point, such as the pinky knuckle may be used as the second reference point.

Figure 18:
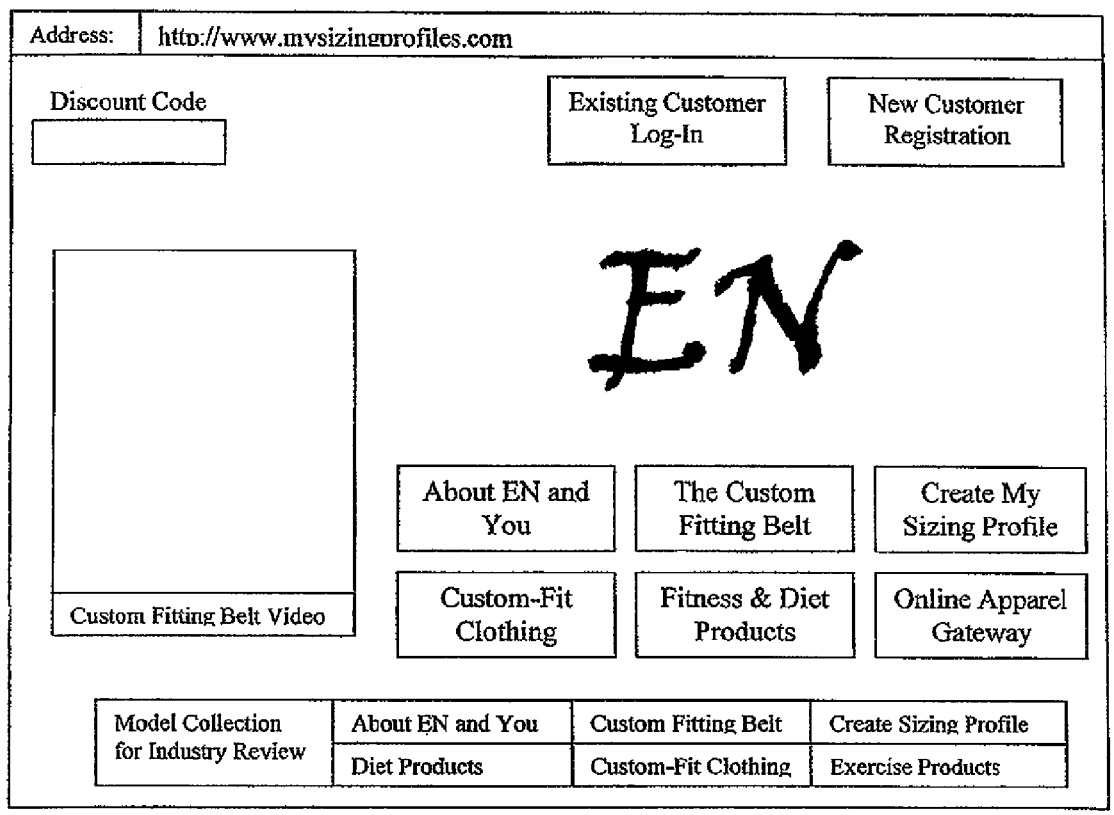
FIG. 18 is a representation of a website home page.

The measurement device may be sold online as well as through other channels. Referring more particularly to FIG. 18, a host website includes a link to "The Custom Fitting Belt" from where a shopper or end user may purchase a custom-fitting belt for taking body measurements. Purchases may be directly from the host as the fitting belt source. The website also includes an icon for "Create My Sizing Profile" where the end user may enter his or her body measurements taken with the custom-fitting belt. The body measurements entered into the website may be tracked by the user as part of a health improvement or exercise program. The website may include records of all previous body measurements of the end user for evaluating progress under the program. The records may be presented as raw data (e.g., in table format) or graphically, such as a chart tracking measurements versus time.

As further shown in FIG. 18, the website also offers other services, including log in and registration functions, information relating to host ("About EN and You"), "custom-fit clothing", fitness products and diet products, and an online apparel gateway. These are only some examples of the myriad of information sources and services that may be offered at the host website.

Figure 20:
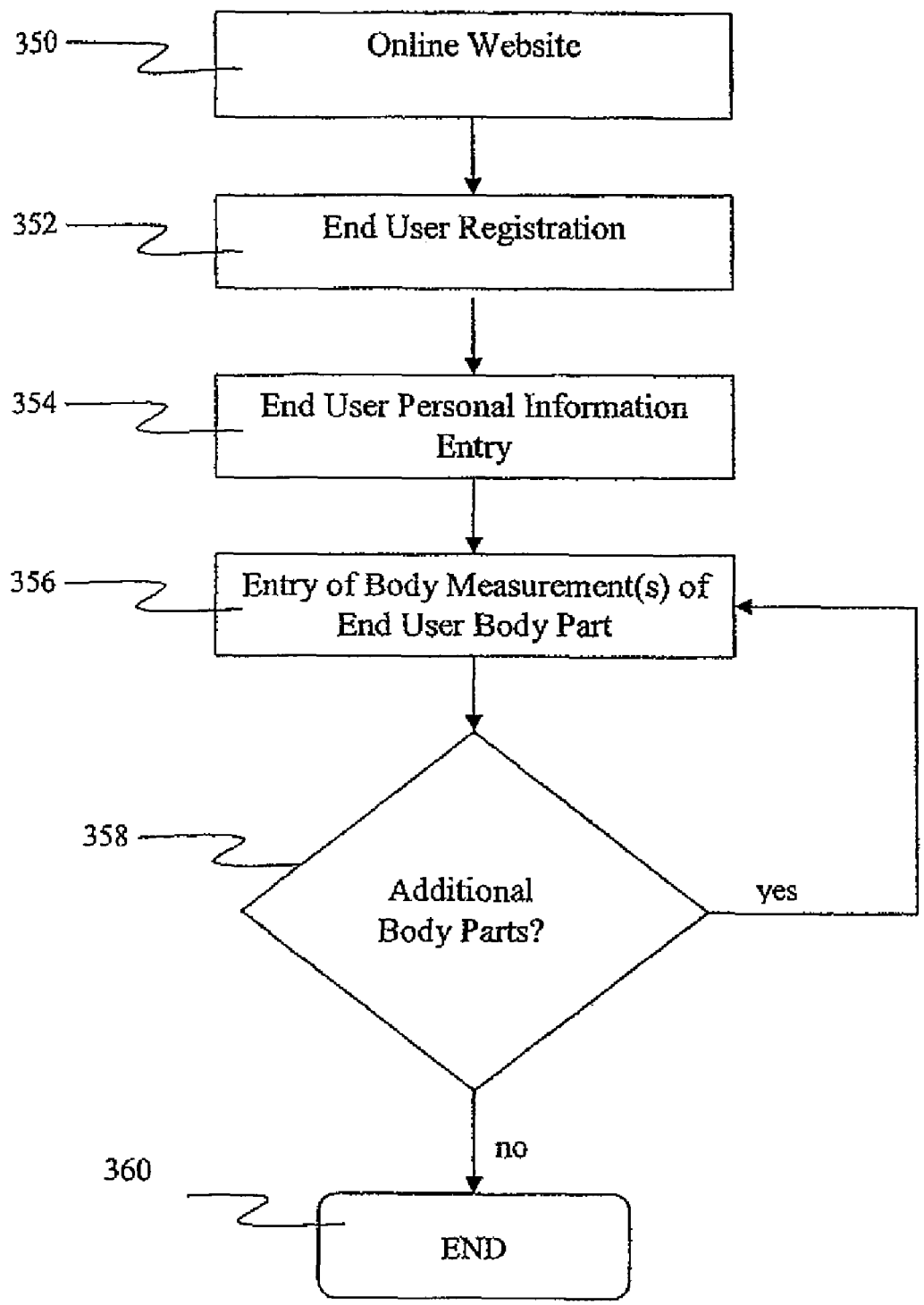
FIG. 20 is a flowchart for registering end users and storing end user information, including body measurement information, according to another embodiment of the invention.

As illustrated in FIG. 20, in an online implementation the end user is logged on to a website 350 and registers 352, as described in greater detail below. Registration 352 may involve the submission of personal information 354. The end user enters the applicable dimensions of a body part at 356. At 358 a decision is made if there are additional body measurements that require entry. If yes, the user is returned to step 356. Otherwise, data entry ends at 360.

As part of the "my sizing profile" service of the website illustrated in FIG. 18, a system and method are provided for virtually rendering a simulated model of an actual body shape and a target body shape of an individual. The body measurement data of an individual are received as described above. A first virtual model rendered to depict the appearance of the individual based on the actual body measurement data is generated. The individual is also allowed to enter target or goal body measurements. For example, an individual having a waist size of 36 inches may wish to see a second virtual model rendered to depict a target appearance of the individual with a 32 inch waist. By selecting and viewing different body measurements, the individual can view different depictions of his or her appearance and decide which body measurements correspond to a desired goal. The first and second virtual models may be displayed simultaneously, such as side-by-side or in superimposed relationship, on an image viewer. Alternatively, the image viewer may show the first virtual model morphing into the second virtual model. Other modes of comparison may also be used.

The online apparel gateway of FIG. 18 is described below with reference to the accompanying drawings. The online apparel gateway comprises a system and method for simplifying and facilitating Internet transactions of garments (wearable articles) for both vendors and shopper/end users, while virtually ensuring delivery of a garment properly size selected or custom fitted to the shopper/end user's satisfaction. As a consequence of this size fitting feature, the shopper/end user is less likely to return or exchange the delivered garment because of an improper fit. The benefits to the vendor and shopper/end user are many fold. The shopper/end user enjoys the convenience and tranquility of online ordering and diminishes the frustrations relating to product returns, such as delays in receiving an exchange or refund, and waiting in line at the post office or private carrier to dispatch the return. The vendor benefits from the shopper/end user's satisfaction of an untarnished transaction, leading to repeat business, and minimizing the erosion of profits caused by product returns. Additionally, the vendor may stock less inventory items and employ fewer personnel at its brick and mortar stores. The bulk of the inventory may be consolidated at warehouses or storehouses for online sales.

The terms garment shopper and garment end user are used distinctly herein. In the illustrated embodiment, the garment shopper conducts the online transaction, whereas the garment end user is the intended ultimate wearer of the garment. As explained in further detail below, the body measurements of the garment end user are used for automatic size fitting or custom tailoring. The garment shopper and end user are one and the same where the garment shopper is the purchaser and ultimate wearer purchasing goods for himself or herself. Alternatively, the garment shopper is not necessarily the ultimate wearer of the garment. The garment shopper may purchase the garment on behalf of a registered end user or as a gift for the registered end user.

Figure 35:
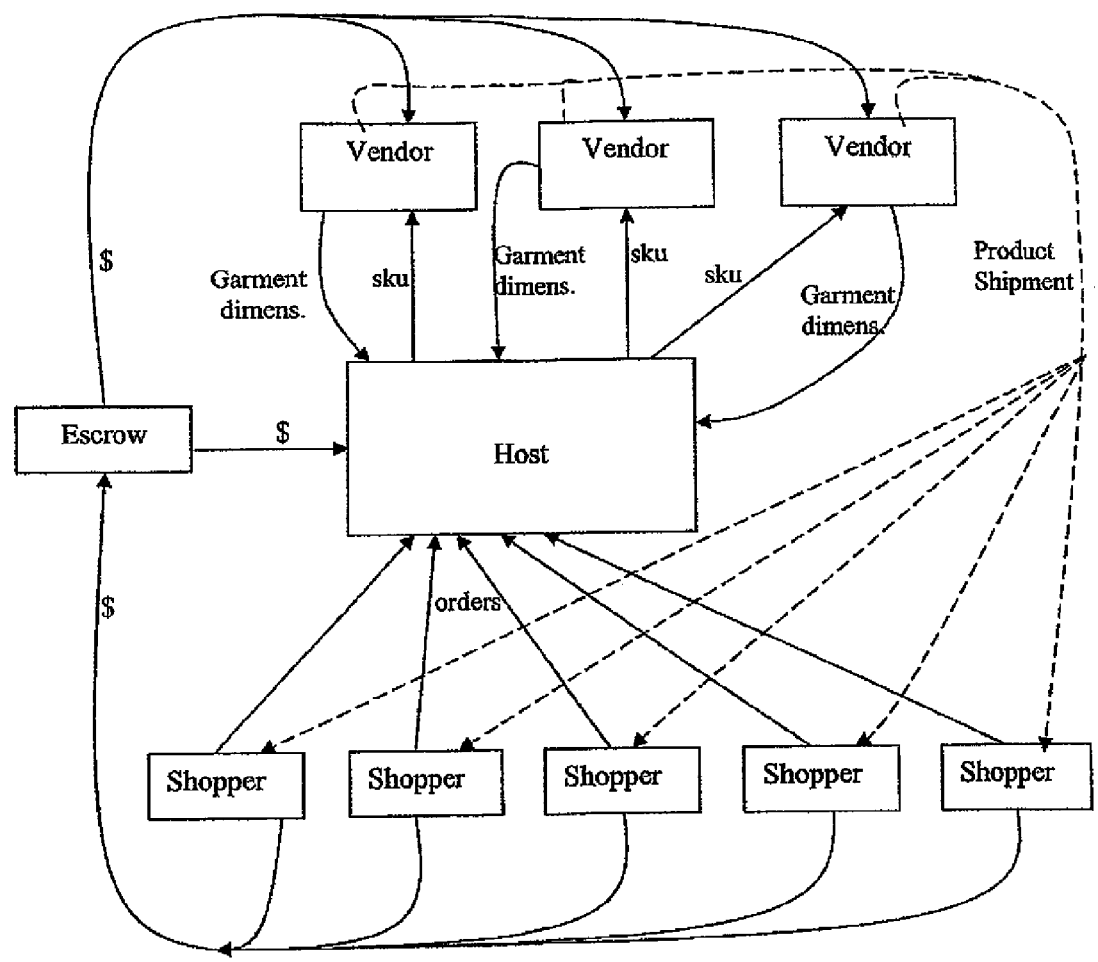
FIG. 35 is a flowchart of a system for online retail garment order processing according to an embodiment of the invention.

In an exemplary constitution of the online apparel gateway embodiment illustrated in FIG. 35, there is a host or principal website from which the garment orders are collected and processed. The host or principal website of a current embodiment possesses the URL or web address mysizingprofiles.com, although it should be understood that other URL designations may be selected. FIG. 18 is an example of a representative homepage that might be found at the website. The host website provides a central online ordering address for at least one or a plurality of product providers. A product provider may be, for example, a merchant, retailer, reseller, distributor, consigner, consignee, wholesaler, importer, exporter, or manufacturer. For the sake of convenience, the terms product provider and vendor are used interchangeably in this specification and the attached drawings. A given product provider may wear multiple hats, e.g., that of a manufacturer, an importer, and a retailer.

The host website effectively operates as an online superstore retailer by offering a single source from which multiple product providers may offer their garments for online shoppers. In an exemplary model, an overview of which is shown in FIG. 35, a host stores in a first database the body measurement data of a plurality of end users (not shown in FIG. 35). The collection of the end user's body measurement data may be tangential or ostensibly unrelated to garment fitting; e.g., the end users' primary reason for submitting its personal information and body measurement data may be to participate in an exercise or health tracking program. Alternatively, end users may furnish their data to the host primarily or exclusively for the purpose of garment fitting and shopping. It should be understood that the personal information and measurement data of the end users may be indirectly submitted to the host, e.g., through a Fitness Center or Broker promoting the use of the host's measuring device and tracking system.

The host stores in a second database the garment dimensions of each garment and garment size of a plurality of vendors. The garment dimensions are preferably obtained directly from the vendor or its manufacturer based on the real pattern specifications used to make the garments. While the terms first and second databases are used herein, it should be understood that the databases may be the same or separate from one another. Further, the first and second databases can be organized or split into multiple databases.

FIG. 35 depicts three vendors or product providers interacting with the host. It should be understood that the system may contain one, two, three, four, or more vendors. In FIG. 35, the arrows pointing from each of the vendors to the host represent transfers of actual garment dimensions and other product specifications of the vendor's garments from the vendors to the host. For garments available in two, three, four, or more sizes, actual garment dimensions will be transferred for each size. The "other product specifications" may include, for example, stock keeping unit (SKU) identifiers, available colors, available patterns, and other indicia. The vendor may deem certain product specifications as proprietary or confidential, and require the host to treat them as such.

The host provides a central location or website at which the garments of each of the vendors may be viewed by shoppers. While FIG. 35 shows a finite number of shoppers (i.e., five), it should be understood that the system may be publicly accessible to all members of the public wishing to purchase online or through some other channel. The shopper may be the actual end user or another individual, e.g., purchasing the garment on behalf of or as a gift for the end user. When a shopper finds a garment of interest on the host's website, the shopper places a purchase order, as represented by arrows pointing from the individual shoppers to the host in FIG. 35.

In addition to identifying the selected garment item or items, the purchase order may include shipping and other information.

The shopper completes the transaction by providing payment information. In FIG. 35, an embodiment is depicted in which payment is made to the host in escrow. The shopper's payment in escrow is apportioned by agreement to the host and vendor or vendors. In an alternative embodiment, payment is made directly to the host (without escrow), who retains a percentage or agreed upon amount of the collected payment, and transmits a percent or agreed upon amount to the appropriate vendor. In either event, the host serves as the de facto payment recipient.

The host accepts the order from the shopper and, upon confirmation of receipt of payment, correlates the order to end user's body measurement data in the first data base. The body measurement data of the end user is matched to the corresponding size garment based on garment size information stored in a second database to automatically select the appropriate size garment. Preferably this sizing decision is made by the host for the shopper. Although not shown, alternatively the host site may notify the shopper of the matching product size and request confirmation that the matched size is acceptable.

Shipment of the product to the shopper or end user may be completed in one of many ways. In the embodiment illustrated in FIG. 35, the host sends instructions or a request to the appropriate vendor to fill the shopper's order. The instructions or request may contain a reference number, such as a stock keeping unit (SKU) associated with the selected product and product size and the shipping address. The vendor ships the product on behalf of the online retailer/host to the shipping address provided by the end user. Alternatively, the host may ship the product directly to the shopper's shipping address, or may employ or contract a third party such as a shipping company or distributor to handle delivery of the garment item to the shopper's shipping address. Essentially, the entire translation is handled or overseen by the online retailer/host.

Both the online shopper and the product provider benefit immeasurably from the use of the host website. Convenience to the online shopper is enhanced because the online shopper is not required to search and maneuver between different product provider websites to compare different products and prices offered by each of the product providers. Further, the online shopper is able to obtain correct size fittings for garments of each of the product providers while registering their body measurements (discussed below) at only the host site. The product provider benefits by exposing its products to Internet traffic at the host site, thereby expanding its marketing channels and widening its exposure to, among others, individuals using the measurement device and sizing profile capabilities of the host website. The product provider is thereby able to reach online consumers that otherwise might not have considered purchasing a garment from a given product provider or located the vendor's website via a search engine. Product exposure is expanded even further if the host website is tied into or associated with health and fitness centers and the like, as discussed herein. An additional advantage to the product provider resides in the cost savings. The product providers are not required to individually collect and process the body measurement information of the end users. Instead, the product provider may rely on the host exclusively for this function.

The measurement devices and practices disclosed herein allows for consistent measuring of body dimensions, resulting in the collection and compilation of extremely accurate data. The database of body measurements itself constitutes a valuable asset that may be used in conjunction with the online apparel gateway of the website to size fit and make retail sales of properly fitting garments to end users having a sizing profile. The host likely will find it advantageous to maintain its end user's personal information and body measurements confidential, even from the product providers. The host can maintain confidentiality by not divulging to the vendor body measurement data and sizing information, apart from a SKU number which has been matched to an end user's order. Additionally, the host's database of user personal information and, more particularly, user body measurements may be useful and valuable for data mining applications. An amassment of body measurements of a sufficiently large group of end users may provide the host with critical information concerning a population's average body measurements and fit preferences. The body shapes and sizes of the general population are constantly changing due to such societal issues as obesity. The collection and updating of body measurements by the host may be used to formulate conclusions concerning the overall characteristics of a given population. These conclusions may be used, for example, to define garment fitting sizes that cover a greater percentage of the population. The host may sell or otherwise provide its conclusions (without divulging the underlying data) to the product providers and others for various purposes, such as revamping the standard fit sizes of a product line to cover a greater percentage of the relevant online garment-purchasing population.

The data mining applications generally do not create security concerns. The data mining analyses usually may be performed by the host without disclosing to the product providers the identities or body measurements of the end users. Consequently, end users made aware of the data mining analyses performed with their sizing information are reassured that the confidentiality and secrecy of their personal information will not be compromised.

Figure 36:
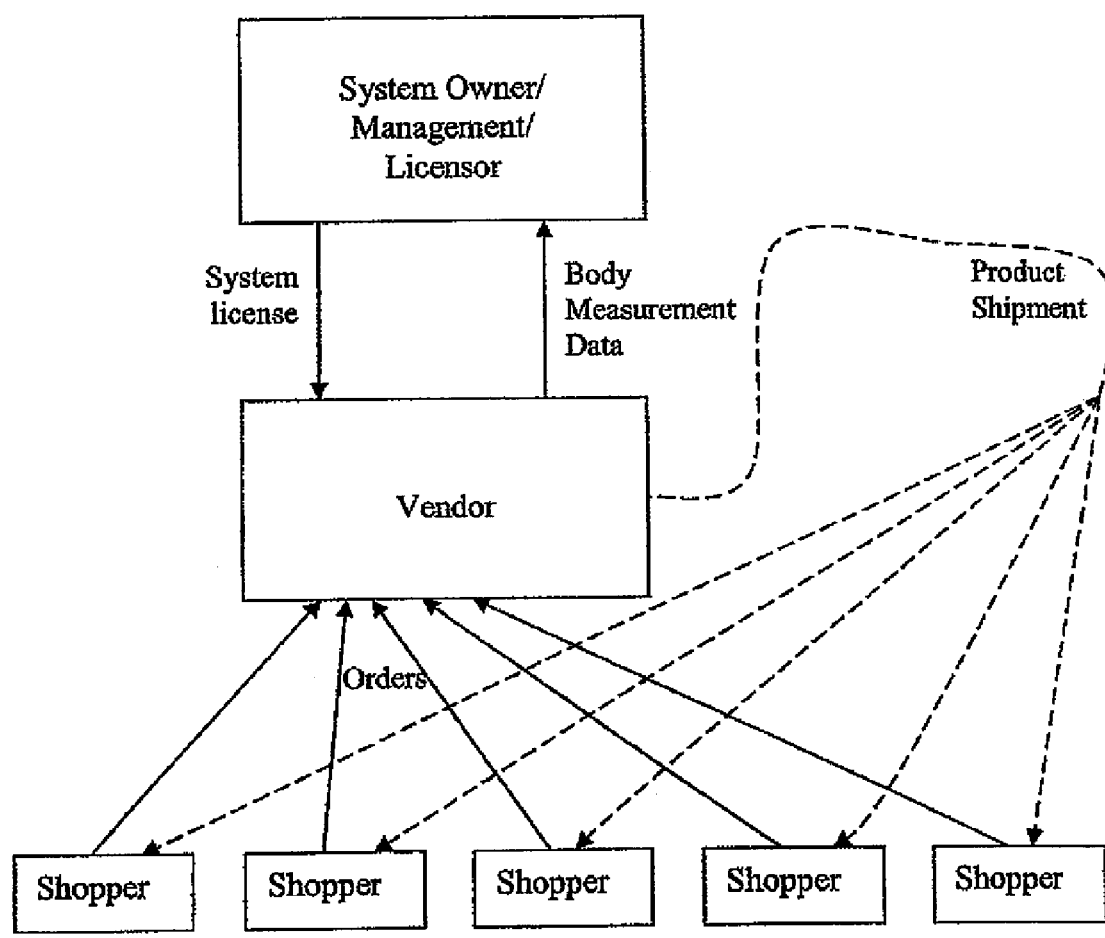
FIG. 36 is a flowchart of a system for online retailer garment order processing according to another embodiment of the invention.

According to another exemplary constitution of the online embodiment depicted in FIG. 36, the owner/manager/licensor of the garment fitting system described herein licenses or otherwise authorizes a product provider/vendor to use its system, including any software, hardware, instructions, or other information necessary to practice the system. Instead of operating through a central host website as in FIG. 35, in FIG. 36 the vendor advertises its garments for sale online at its own online website, and offers an automatic size fitting feature for online purchases. The vendor website may possess a web address or URL integrating the vendor's name. As above, a product provider or vendor may be, for example, a merchant, retailer, reseller, distributor, consigner, consignee, wholesaler, importer, exporter, manufacturer, etc. The garment provider receives garment orders and payment from shoppers, and processes the order directly without the intervention of a host. In an exemplary model, the vendor registers its own end users, and retains the personal information of the registered users for its own uses, such as for compiling a client list for sending marketing materials either online or by mail. The vendor may share the body measurements of its ends users with the owner of the garment fitting method and system for data mining purchases. The structure of this arrangement between product provider and owner is advantageous to both parties. The product provider avails itself of the owner's garment fitting method and system, while maintaining valuable lists of end users and their personal information as trade secrets. In return for use of its system, the vendor provides the owner/licensor with the body measurement information of its customers, thereby broadening the owner/licensor's population of body measurement information for data mining applications.

Figure 15:
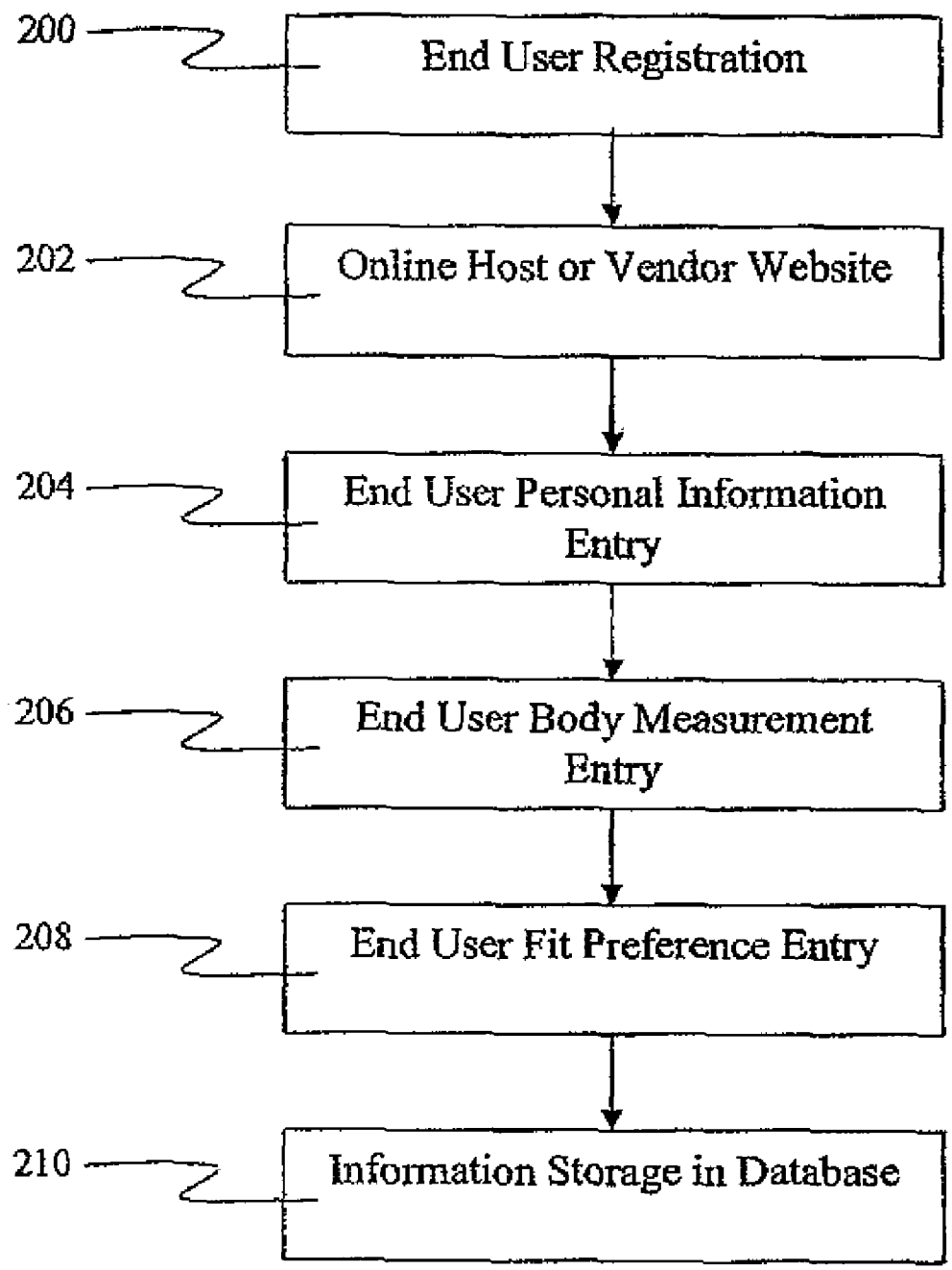
FIG. 15 is a flowchart for registering end users and storing end user information according to an embodiment of the invention.

A registration flowchart for populating a first database in which user body measurement information is stored is illustrated in FIG. 15. End user registration 200 is performed by logging on a host or vendor website at 202. The end user may register themselves or may be registered by a third party. Self-registration may be accomplished at a product provider's brick and mortar store or at the convenience of the end user's home or other selected locale having an Internet connection. Body measurements are preferably taken with the measuring device described below. Instructions for taking body measurements useful in selecting standard fit sizes may be furnished with the measuring device. The website may include downloadable instructions for assisting the end user in properly taking his or her body measurements. Alternatively, the end user may seek the assistance of a third party, such as a Fitting Center or a Broker, trained in taking body measurements with the custom sizing belts. A Fitting Center is, for example, a vanity oriented shop, salon, spa, or gym for marketing and selling custom-fitting sizing belts, registering accounts, and providing measuring services. Brokers are individuals or entities that contribute to a secondary marketing channel that adds to the list of registered end users by providing registration and measurement services using custom-fitting sizing belts. Fitting Centers and Brokers may earn commissions or may structure other payment arrangements with the host and/or vendors for registering end users.

At 204, personal information is entered and stored in a first database. The personal information may include a log-in name and password (e.g., personal identification number (PIN)), the name and address of the end user, telephone numbers, email addresses, charge information such as credit and debit card accounts, and shipment and billing addresses. Password protection is well known in the art, and is particularly desirable for end users in view of the sensitive nature of the body measurements and other personal information stored in the system. Password protection limits accessibility to the end user's sensitive personal and body measurement information to persons and entities possessing the password or otherwise granted permission. Hence, for example, the body measurements of an end user would not be divulged to a gift shopper purchasing a garment for the end user. The host optionally may structure its license with the end user to permit use of the stored personal and/or body measurement information for data mining and other purposes.

At 206, the end user enters-his or her body measurements obtained with a measurement device featuring a belt having a first scale of first measurement indicia and a strap having a second scale of second measurement indicia. The strap has a strap end attached to the belt. A custom fitting belt and size measurement techniques are described below in detail and disclosed in U.S. Pat. No. 7,249,423 and U.S. patent application Ser. No. 11/878,753, the complete disclosures of which are incorporated herein by reference. A first body measurement is obtained from the belt placed at a first position on the end user and a second body measurement is obtained from the strap while the belt is maintained at the first position. The body measurements may include, for example, circumference measurements such as for the head, neck, biceps, forearm, wrist, ankle, calf, thigh, buttocks, waist, and chest. Other design specifications may include rise, pant length, ½-shoulder, and sleeve length.

The end user fit preferences are entered at 208. The fit preferences include the types of fit that the client prefers. Fit preferences may range from baggy to tight, with various levels in between, such as loose, relaxed, standard, athletic and snug. It is within the scope of the invention to permit the end user to assign different fit preferences for different clothing items. For example, the end user may prefer loose pants but athletic fit shirts. Certain personal fit preferences may be adequately captured through the use of the exemplary custom fitting belt described herein. By way of example, an end user who prefers to wear pants lower or higher than intended by the garment designer may seize the preference by positioning the belt at a first position corresponding to the desired waist line location of the garment.

The entered information is stored in a first database 210, which the end user may access thereafter to update his other body measurements. It is not unusual for end users to experience weight changes and fluctuations as they age. Updating the body measurements stored in the first database ensures that garment sizing recommendations stay current and accurate over time. Optionally, the system may generate a reminder to the end user to update their body measurements periodically, such as annually. The reminder may be disseminated by email, for example. The periodic entry of updated body measurements provides the end user with a record of body measurement changes. The utility of the database as a health tracking tool provides a strong tie-in with Fitness Centers. The embodied method and system described herein may be marketed through the Fitness Centers as a multifunction tool both for improving garment size fitting and for quantitatively tracking physical improvements, e.g., body measurement reductions, achieved through training at the Fitness Center.

Figure 16:
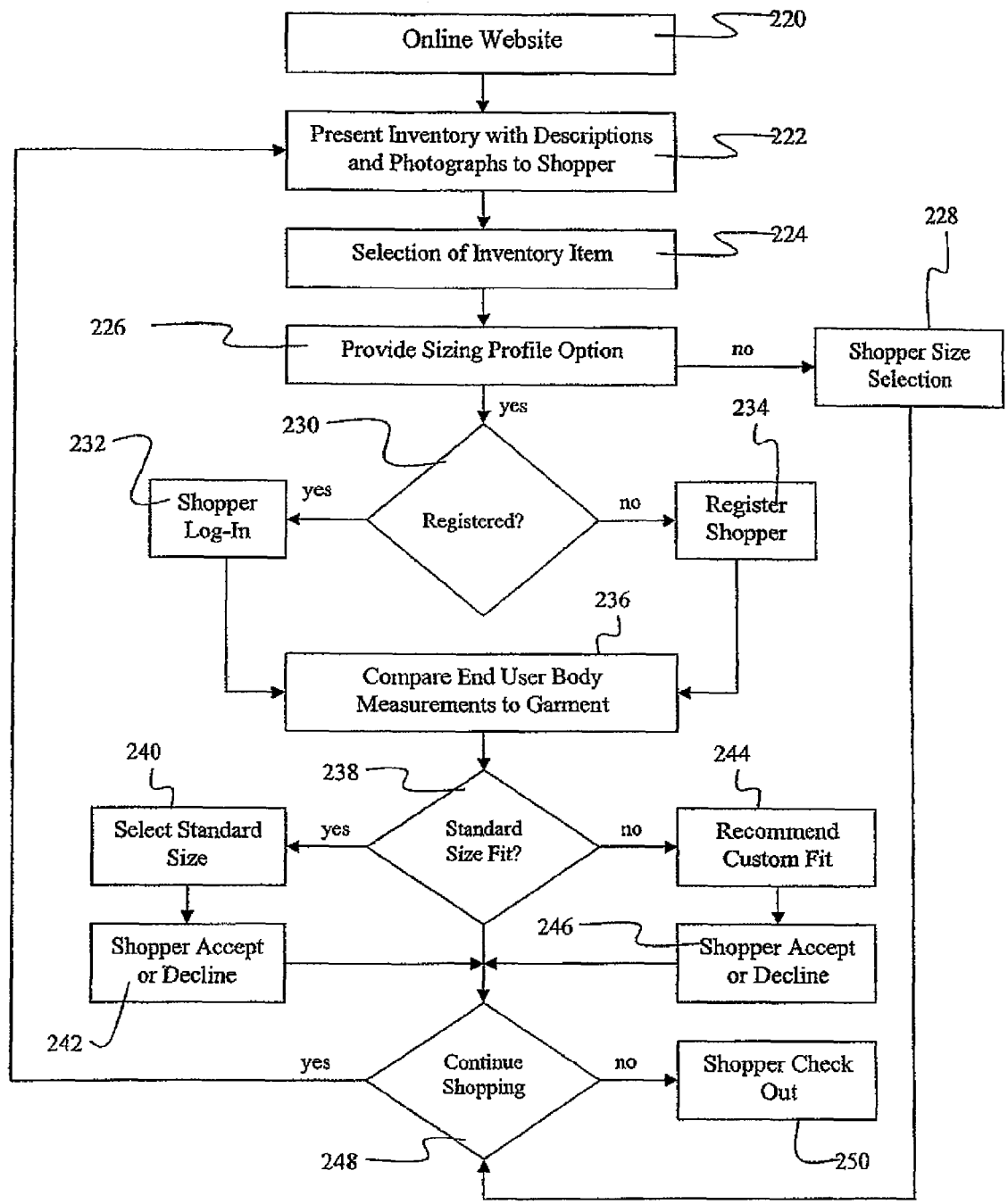
FIG. 16 is a flowchart for carrying out online shopping according to an embodiment of the invention.

Referring now more particularly to the online embodiment illustrated in FIG. 16, a garment shopper logs onto the Internet and selects or searches for a host or vendor website at 220 to shop online. Online shopping may be performed remotely by the garment shopper. For example, the garment shopper may be able to place the order from home or another locale without actually visiting the host or vendor's brick and mortar store. Additionally, one or more online shopping computers or kiosks may be installed on the premises of the brick and mortar store to allow the shopper to locate and purchase garment items missing from or otherwise not in inventory at the store. The presence of online shopping computers or kiosks available in a store may be particularly useful during busy shopping times when the in-store shoppers outnumber the salespersons. Rather than waiting impatiently for a salesperson to become available, the in-store shopper can obtain automated assistance at the kiosk.

The host's or vendor's inventory is stored in a second database accessible by the garment shopper at 222 via a web browser. As is known in the art, the inventory may be organized by categories, such as by gender (e.g., men, women, boys, girls) and apparel group (e.g., pants, shirts, dresses, suits, skirts, blouses, shorts, etc.). Other category descriptors may be used, such as apparel style, e.g., formal, casual, etc., or special sizing, e.g., big and tall.

Figure 17:
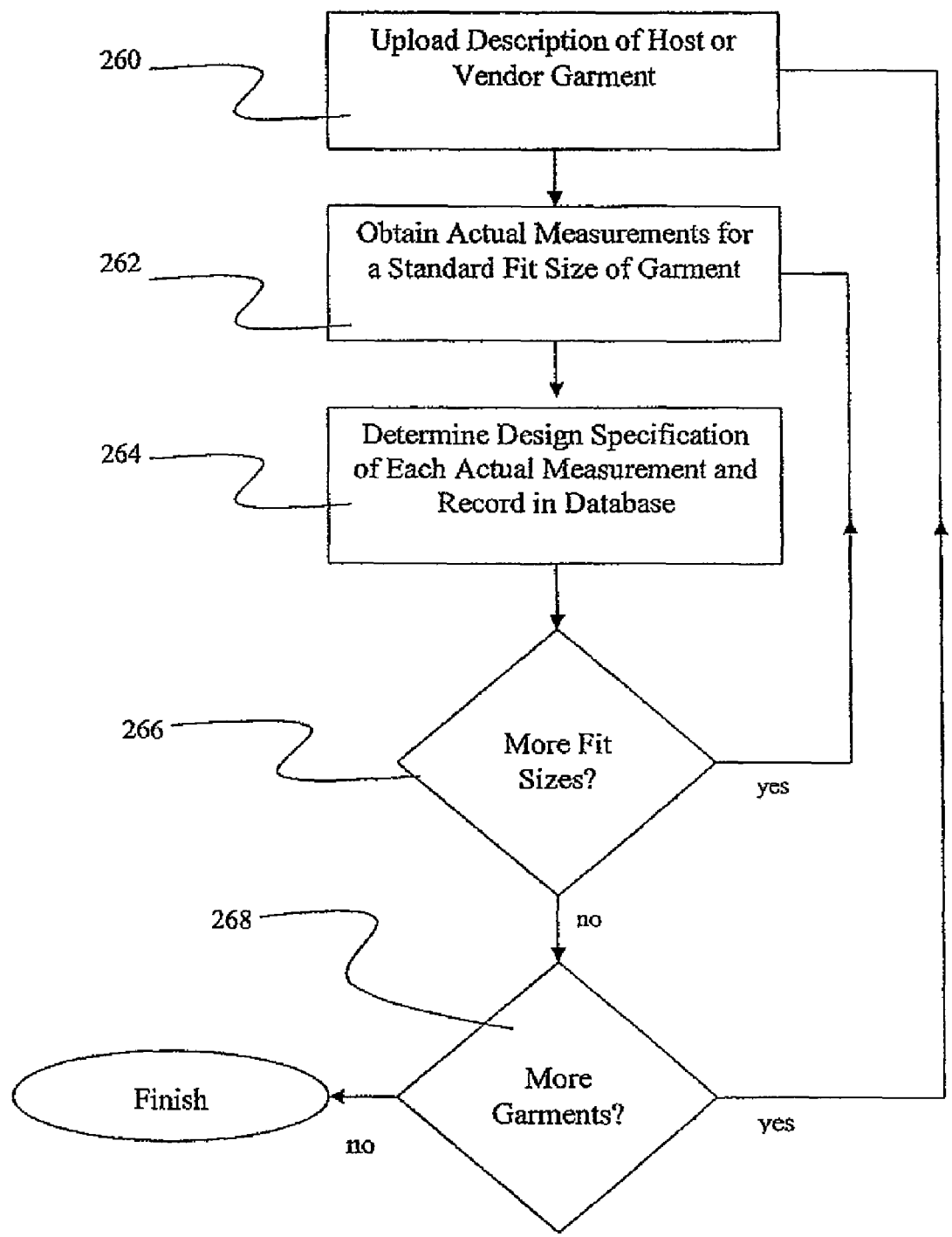
FIG. 17 is a flowchart for recording and storing design specifications of garments according to an embodiment of the invention.

FIG. 17 is a flowchart illustrating an embodiment for populating a second database with the inventory of one or more vendors. At 260, a description of a garment of the inventory is uploaded by the host or on the host's behalf (e.g., by the vendor) into the second database. The description may include a characterization of the style and features of the garment, the material from which the garment is made, and its country of origin, among other information. The description may further include a digital photograph of the garment or a model wearing the garment. The description may contain other helpful information, such as a selection of patterns and colors in which the garment is available, and product identifiers, e.g., SKU numbers.

At 262, the actual garment measurements are obtained and recorded. The actual garment measurements for a standard fit size generally differ from one product line to another. Accordingly, to ensure optimum fit selection of a standard size garment of a particular product line on an individual end user, the actual measurements of each of the garments are obtained and populated into the second database. The garment designer and manufacturer are contemplated sources of the actual garment measurements. To ensure accurate measurements, the pattern specifications used in making the garment may be selected as the actual garment measurements. Alternatively, the actual garment measurements may be determined by the host, such as by reverse engineering, e.g., disassembling a garment into its constituent pieces, to obtain the actual measurements. The measurements may include, for example, circumference measurements such as of the head, neck, chest, biceps, forearm, wrist, waist, buttocks, thigh, calf and ankle, and length measurements, such as rise, pant length, ½ shoulder, and sleeve length.

Because the actual body measurements of an end user will rarely exactly match all of the exact actual garment measurements for a particular garment, it is desirable in certain embodiments of the invention to broaden each of actual garment measurements into a broader range or set of "design specifications" for matching with the actual body measurements. Design specifications are, for example, ranges constituted by or determined from the actual garment measurements, and are recorded at 264. The design specifications are selected to provide reliable evaluation as to whether a particular garment standard fit size is suitable for a particular end user. The range may be ascertained, for example, by application of an acceptable tolerance or scaling factor to the actual garment measurement.

The usefulness of determining design specifications is explained through the following example. A standard medium size pair of short pants for a particular vendor's garment may have an actual waist circumference of 34 inches. Rather than requiring that the end user have an exact waist measurement of 34 inches to qualify as a proper fit of the medium size pants, the waist measurement may be converted into an acceptable tolerance range of waist sizes that an end user should possess to comfortably or otherwise acceptably fit in the pants. A determination of what is a comfortable or acceptable fit may be made by the garment designer, manufacturer, or vendor, among others. The design specifications may be ascertained by the actual measurements and a scaling factor, such as up to plus 5 percent, in which case the waistband will be deemed to properly fit an end user having a waist of about 32.3 inches to about 34 inches. If the waistband is flexible, the design specifications may range even greater, such as 32 inches to 36 inches. An end user having a waist falling within the design specification range is considered to fit the garment, at least with respect to waistband.

In determining the design specifications, allowances may be made for the personal fit preferences of the end users. It may be the personal fit preference of the end user to wear tight or loose fitting apparel Representative personal fit preferences from which a garment end user may select may include baggy, loose, relaxed, standard, athletic, snug and tight, with various levels and descriptors available. The scaling factor or acceptable tolerance range may be fine tuned based on the personal fit preference of the individual end user. For example, for an actual measurement waistband of 34 inches, the design specifications for an end user having a personal preference for a tight fit may range from 33.5 to 34.5 inches, whereas the design specifications for an end user having a loose fit personal preference may range from 32 to 33.5 inches.

Once the design specifications for a standard fit size of a garment are recorded, a decision is made at 266 as to whether there is an additional standard fit size for that garment. If yes, steps 262 and 264 are repeated for each additional fit size until all of the designs specifications for each standard fit size of the garment are recorded for storage in the second database. Once all of the design specifications for each standard fit size of a given garment are recorded, the process is repeated at 268 until design specifications for each standard fit size of all of the garments in the entire inventory have been recorded for storage in the second database. The second database may be edited as needed to reflect garment changes, and also may be updated to add new garment items introduced into inventory and to remove discontinued garment items and/or fit sizes.

Returning to FIG. 16, at 224 the garment shopper searching the inventory at the host's website is able to select a garment item for online purchase. At 226, a sizing profile option is automatically made available to the garment shopper. Optionally, the garment shopper may decline the sizing profile option and proceed with an unassisted size selection of the garment at 228. Alternatively, the garment shopper may select to inquire about a recommended standard fit size of the selected garment.

The garment shopper is prompted at 230 to identify whether the end user is new or registered. If the end user is already registered than the garment shopper logs in at 232. Log in may be accomplished by entering the end user's log-in name or other personal information sufficient to identify the end user from the first database. Account information, including confidential body measurements and billing information, is not accessible to the garment shopper unless the shopper enters the password. If the end user is not registered, at 234 the online shopper/end user is taken through the registration process as described above in connection with FIG. 15. These steps may be bypassed if the shopper has already registered and logged in, e.g., prior to garment selection or while previously selecting another garment.

At 236, the body measurements of the individual garment end user are compared to the design specifications of the standard fit sizes of the selected garment. A decision is made at 238 as to whether any of the standard fit sizes adequately fits the end user. The evaluation of whether or not a standard fit size is appropriate for an end user may be carried out by comparing the end user's body measurements to the corresponding design specifications of the selected garment. For example, if each of the end user's body measurements falls within the corresponding design specifications of a standard fit size of the selected garment, then the standard fit size is selected at 240. Tolerance (or leniency) with respect to one or more of the design specifications may be applied in making the decision at 238. For example, a standard size fit may be recommended if a limited number, e.g., one or two, of the body measurements do not match the design specifications. In this regard, the design specifications may be weighted relative to one another by importance of fit.

In addition to selecting a standard fit size to the garment shopper, the garment shopper may be presented with a virtual image of the end user wearing the garment in the selected size. For example, the selected fit size garment may be superimposed over a body image of the end user to simulate physically how the garment would drape on the end user. The body image may be proportioned to correspond to the end user's body measurements. The virtual image presentation is automatically performed by the computer system and viewable on a monitor display. Optionally, the virtual image may also include other characteristics of the shopper, such as a digital representation or photograph of the end user's face. Optionally, at 242 the shopper is prompted to accept or decline the fit size selection. Also optionally, the shopper is provided with the capability to modify the virtual image to reflect the end user's "target" body measurements. In this manner, the shopper is able to determine how the garment will fit after the end user has completed his or her dieting or body shaping program.

Returning to 238, if the end user's body measurements cannot be matched adequately to any of the standard fit sizes, the garment shopper is offered a custom fit option at 244. Although not shown in the flowchart, the custom fit option also may be offered if the shopper declines a selected fit size. More discerning customers willing to bear the added expense of a custom-fitted garment may wish to avail themselves of the customization option even when a standard stock size might be selected. The shopper is allowed to accept or decline the custom fitting option at 246.

If accepted at 246, the body measurements of the end user are used to generate a custom-fit garment. For example, the body measurements may serve to establish pattern points on a roll of material (e.g., cloth, leather) from which the custom tailored garment is to be made. The pattern points define the shape of a piece of the garment, and serve as a guide for cutting a roll of material to generate the garment pieces. Alternatively, the body measurements may be used to provide alteration suggestions to one of the stock size patterns. The standard size fit closest to the body measurements of the end user is selected as a starting point for the alterations. The pattern points of the closest standard size fit are altered to customize the garment for an individual, and the garment pieces are cut from a roll of material using the altered specifications. Assembly of the garment pieces into a custom garment may be carried out by automated machinery and/or by a tailor or other skilled operators. The above-described virtual imaging capability may be employed to design the custom garment to the end user's preferences.

At 248, the garment shopper may select to continue shopping, in which case the shopper is returned to the inventory at 222 in the flowchart. If the shopping session is complete, the shopper is advanced to checkout 250.

Figure 19:
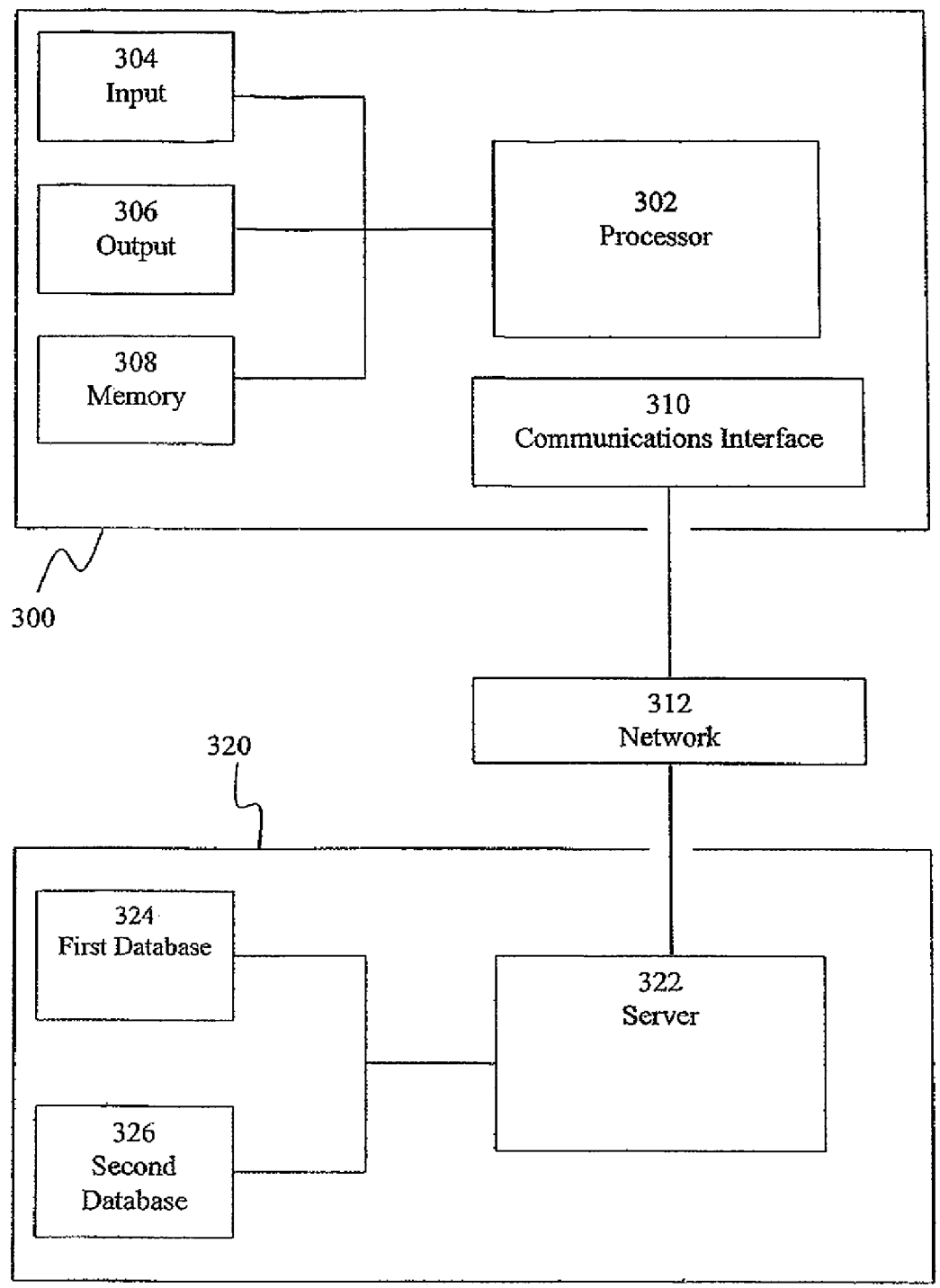
FIG. 19 is a diagram of a system suitable for carrying out embodied methods of the invention.

FIG. 19 is a diagram of an exemplary computer system of an embodiment of the present invention. The computer system comprises a remote user interface terminal 300 from which a garment shopper may place an order and/or from which a garment end user may enter or have entered his or her personal information and body measurements. Terminal 300 may be a personal computer with a central processing unit (CPU) processor 302, such as a PENTIUM or CELERON processor. Examples of other suitable remote user interface terminals 300 include held-held devices, Web pads, smart phones, interactive television, interactive game consoles, two-way pagers, e-mail devices, equivalents, etc. While a single remote user interface terminal 300 is shown in FIG. 19, it should be readily understood that the system may comprise multiple remote user interface terminals located at, for example, the domiciles of the end users or shoppers, the Fitness Centers, the Broker's places of business, the Product Providers' brick and mortar stores, public kiosks, etc. It is possible to configure terminal 300 as a "dumb" terminal where the CPU processing is carried out remotely, e.g., at a server 322.

Processor 302 communicates with input device 304 and output device 306. Input devices 304 suitable for terminal 300 include, for example, keyboards, numeric or alphanumeric keypads, pointing devices (e.g., a mouse), imaging equipment, touch-sensitive pads, joysticks, voice recognition systems, combinations thereof, and/or other equivalent or known devices Input device 304 generates signals in response to physical, oral, or other manipulation by the end user or shopper and transmits those signals to processor 302. Output device 306 presents information to the end user and shopper. Output device 306 may include a display screen, such as a commercially available monitor, light-emitting diode (LED) display, or liquid crystal display (LCD). Output device 306 additionally or alternatively may include any other mechanism or method for communicating with the end user and shopper, such as, for example, an olfactory, visual (e.g., printer), audio (e.g., speakers), audio-visual, or other sensory device. Terminal 300 may further include other features and components not shown, such as a sound card and/or a video card.

Remote user interface terminal 300 further includes a memory 308 in communication with processor 302. Memory 308 may include random access memory (RAM) (e.g., 256 MB of RDRAM), read-only memory (ROM), and storage device(s) such as hard disc drives and storage media, for example, optical discs and magnetic tapes and discs. The illustrated system further includes a communications interface 310 for communicating with a transmission network 312 such as the Internet. Communications at interface 310 and over transmission network 312 may include wireless connections, such as microwave, radio frequency, and laser technologies. Connections to the Internet may be made directly or through Internet Service Providers (ISPs).

Communications interface 310 and transmission network 312 connect user interface terminal 300 to a host or vendor sub-system 320 including a server 322, a first database 324 and a second database 326. Server 322 may carry out various processing functions described above and depicted in FIG. 16, including for example comparing the body measurements of the individual end user to design specifications of a garment item and providing the garment shopper with at least one of the recommended standard fit size for the selected garment item and a customization option for the selected garment item.

Figure 3:
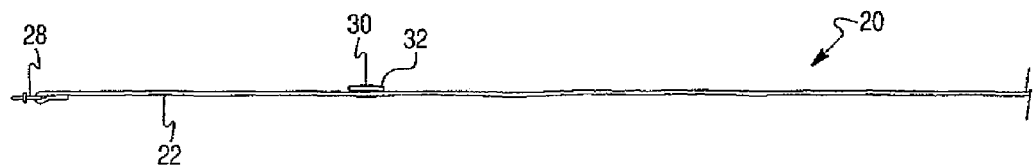
FIG. 3 is an end view of the measuring device of FIG. 1.
Figure 4:
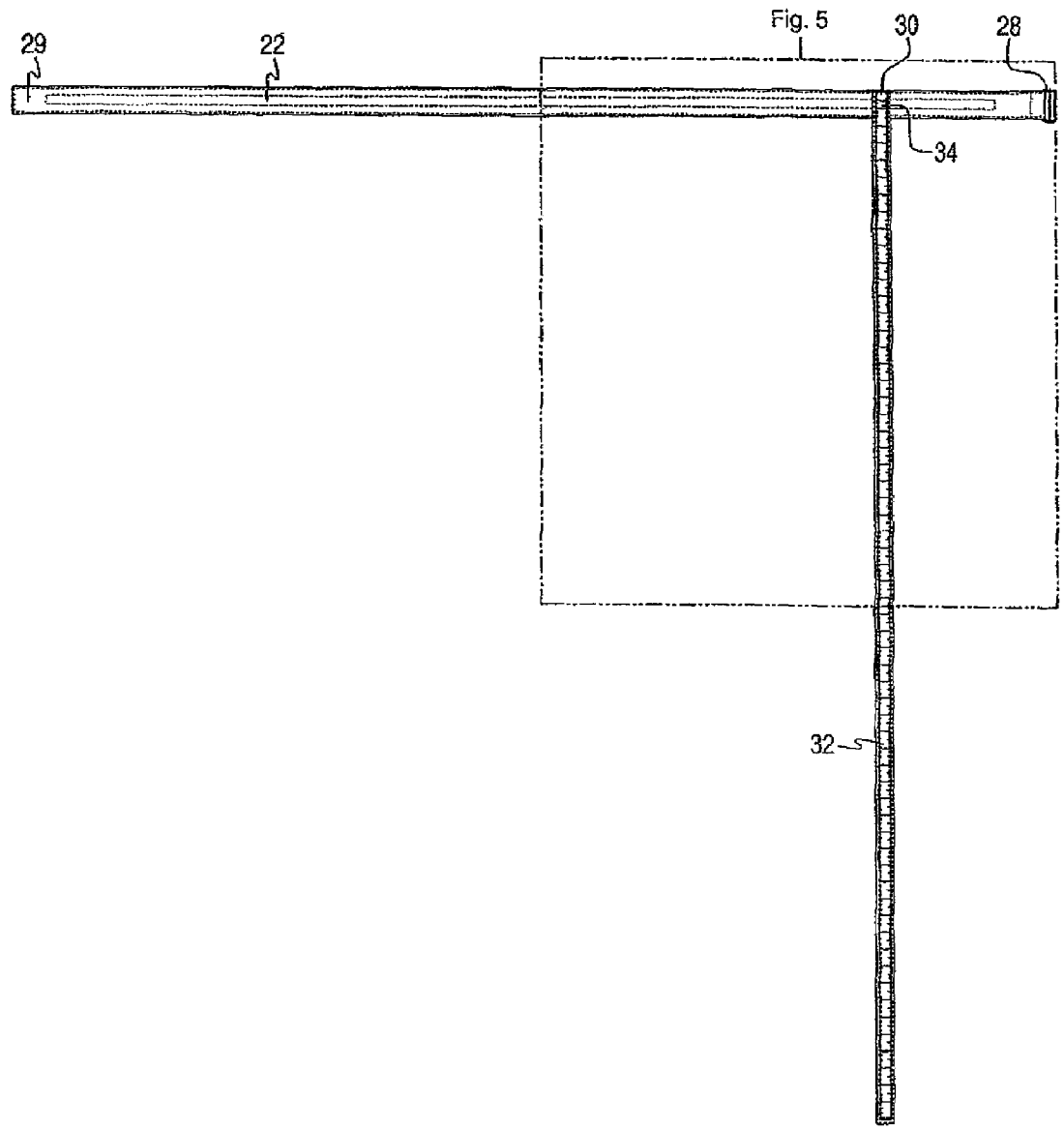
FIG. 4 is bottom view of the measuring device of FIG. 1.

An exemplary embodiment of a measuring device for obtaining end user body measurements for storage in the first database is generally referred to by reference numeral 20 in FIGS. 1, 3, and 4. Measuring device 20 may be disseminated, e.g., sold, to end users through different channels, including the host, product providers, Fitness Centers, and Brokers. Instructions for using measuring device 20 and carrying out the measurements discussed below may be disseminated with measuring device 20 or downloadable over the Internet from either the host or vendor website.

Figure 2:
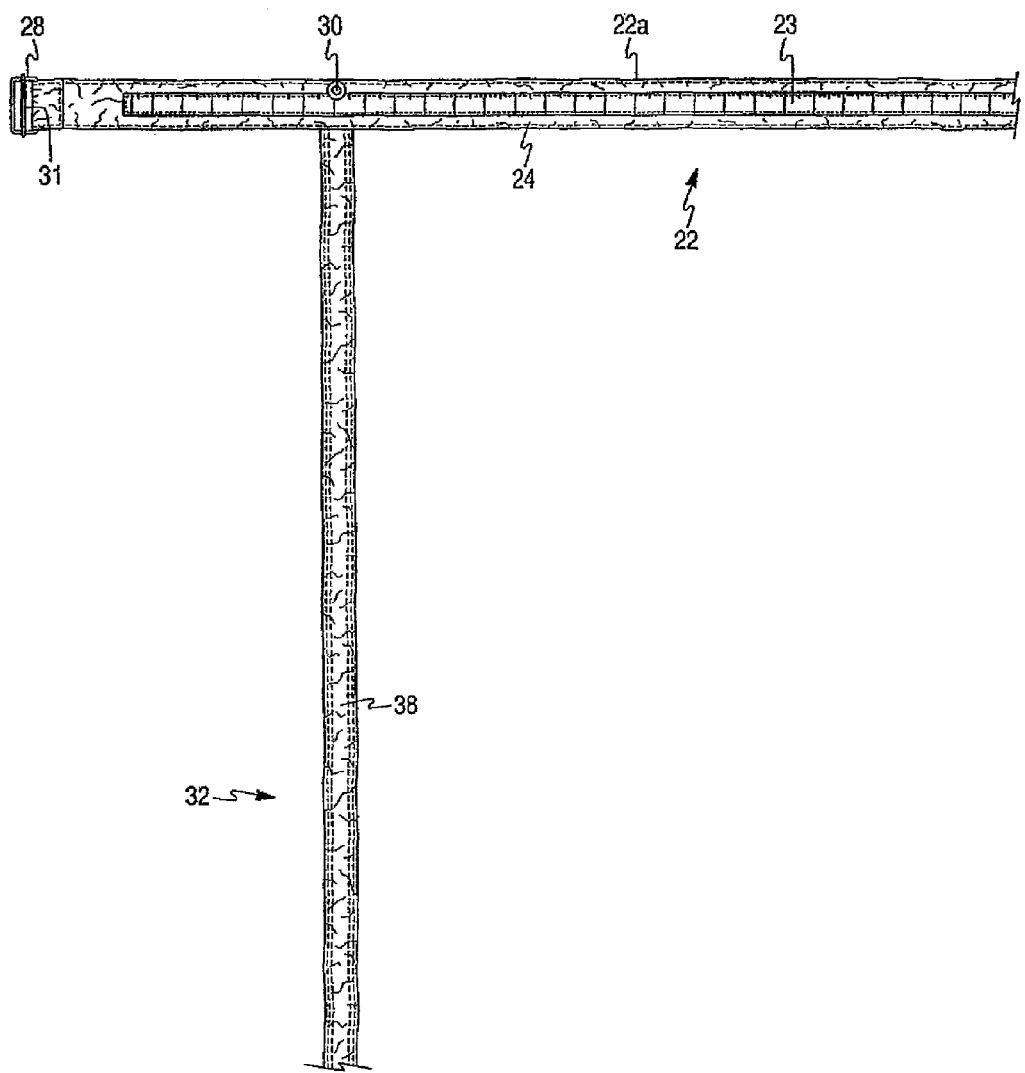
FIG. 2 is an enlargement of a portion of the view depicted in FIG. 1.
Figure 5:
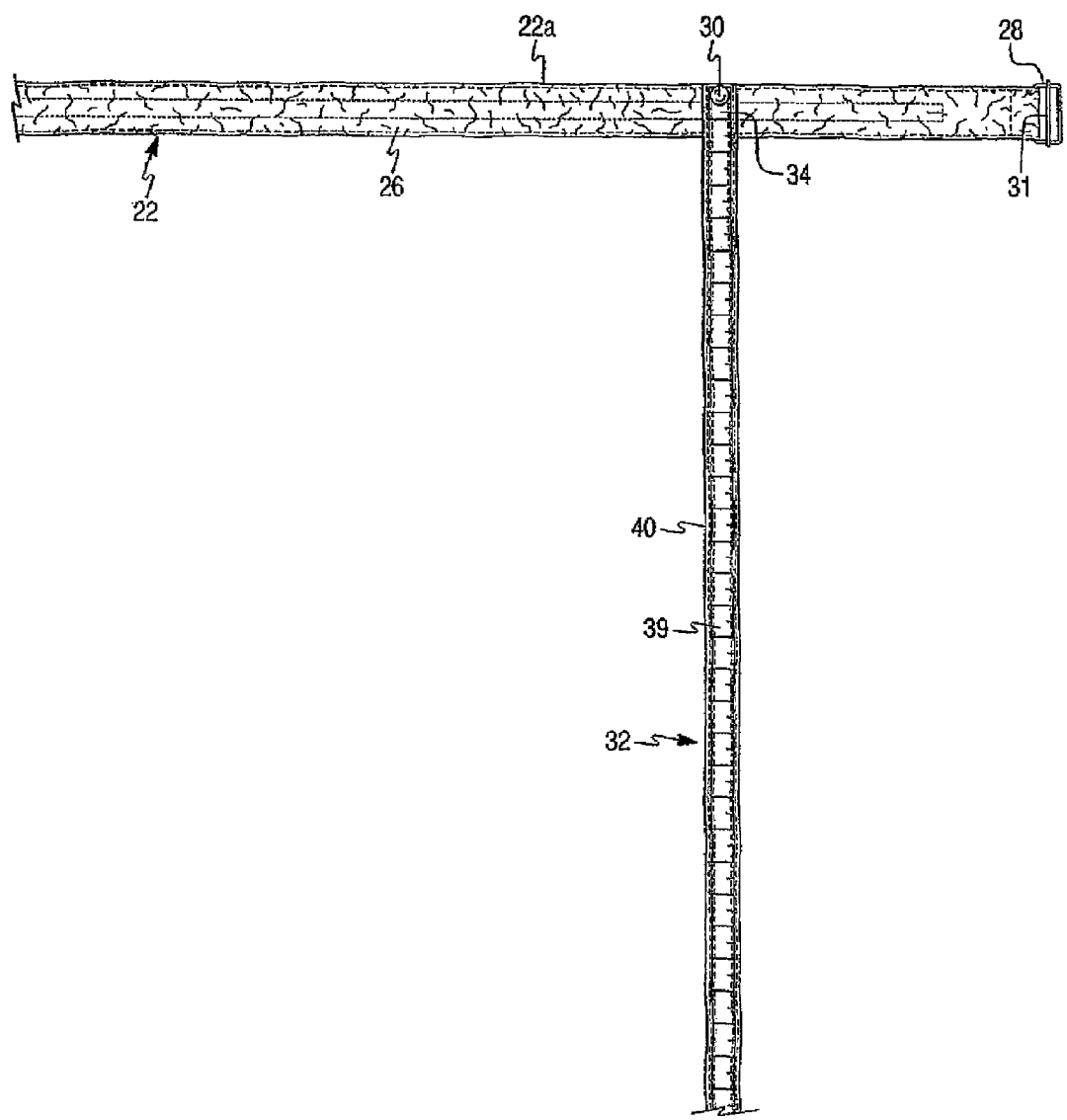
FIG. 5 is an enlargement of a portion of the view depicted in FIG. 4.

Measuring device 20 features a belt 22 having a flexible belt body capable of being encircled about a body part of an individual, such as around a waist, neck, chest, arm, thigh, hip and/or head. The belt body has an inner face 24 (FIG. 2) and an opposite face 26 (FIG. 5). A buckle 28 is provided at one end of belt 22, and is sized to permit feeding of the opposite second end 29 of belt 22 through buckle 28. Attachment of buckle 28 to belt 22 may be accomplished in known manners, such as by folding over sewing excess belt length to create a loop securing buckle 28. As discussed in further detail below, belt 22 further comprises a fastener 30, which in the illustrated embodied device 20 comprises snap halves.

The inner face 24 has a belt scale 23 of measurement indicia for providing circumference measurements. The scale 23 may comprise a measuring tape, marking strip, etc. attached to, e.g., sewn into, the body of belt 22. Alternatively, the first scale may be embedded, integral with, marked on, or otherwise associated with the belt body. In the illustrated embodiment, the opposite face 26 of the belt body does not include a scale of measurement indicia. It should be understood, however, that it is within the scope of the invention to include a separate scale of measurement indicia on the face 26, and to make the scale of measurement indicia of the face 26 identical to or different from the indicia of the first scale on the inner face 24.

The belt scale 23 may be in a measurement scale of inches, centimeters, etc., and may be broken down or graduated into smaller units, e.g., eighths of inches, millimeters, etc. Alternatively, the inner scale may comprise a different scale or symbols, such as, for example, indicators for small, medium, large, extra large, or women's sizes (e.g., 2, 4, 6, etc.). These are just examples of measurement indicia that may be used. The inner scale of measurement indicia employs the end of buckle 28 as a reference starting point for measuring distance along the belt 22.

Measuring device 20 further comprises a strap 32 having a strap end 34 attached fixedly to the belt body. The fixed attachment is accomplished using fastener 30, which is illustrated in this embodiment positioned in relatively close proximity to buckle 28. In the illustrated embodiment fastener 30 is depicted as a snap pair, i.e., a first half of the snap pair integrated into belt 22 and a second half of snap pair integrated into strap 32. The snap pair fastener 30 fixes the connection between belt 22 and strap 32, inasmuch as fastener 30 renders the attached strap end 34 non-slidable along the length of the belt 22.

It should be understood that other types of relative movement between belt 22 and strap 32 are not necessarily restricted by fastener 30. For example, according to one exemplary embodiment snap pair fastener 30 creates a pivot point for permitting strap 32 to pivot rotationally about its point of attachment to the belt 22. It should be understood that other types of fasteners may be used in addition to or in place of the depicted snap pair. For example, fastener 30 may comprise Velcro® or other similar commercially available material comprising hook and loop fasteners, buttons, clasps, etc. Fastener 30 is repeatedly detachable from and re-attachable to belt 22 without damage to belt 22 or strap 32 to permit detachment and re-attachment of fastener 30 from belt 22, even when belt 22 is encircled upon itself with the belt second end 29 fed through buckle 28.

Fastener 30 provides additional advantages over prior known constructions which attached a strap to a belt through a loop-type connection. These prior constructions were prone inaccurate measurements since, as the strap was tensioned, it would tend to bend or pull the looped section of the belt out of alignment. With the construction of the fastener 30 of the present invention, the fastener 30 can be designed to automatically uncouple the strap 32 from the belt 22 under a pre-selected amount of tension, e.g., in the event undue tension is applied to the strap 32 that might have a tendency to bend or move the belt 22 out of a true and accurate position or alignment.

Strap 32 has an inner face 38 (FIG. 2) and an opposite outer face 40 (FIG. 5). In the illustrated embodiment, in FIG. 5, outer face 40 features a strap scale 39 of graduated measurement indicia. The attachment of strap end 34 to belt 22 as shown arranges the outer face 40, and hence the scale 39, in an opposite direction (facing away) from the scale 23 on inner face 24 of belt 22. In the illustrated embodiment, the inner face 38 of strap 32 does not include a scale of measurement indicia. It should be understood, however, that it is within the scope of the invention to include a separate scale on the face 38, and to make the measurement indicia of the scale associated with the face 38 identical to or different than the indicia of outer face 40.

The strap scale 39 may be the same as or different from the belt scale 23. The strap scale may be a measurement scale of inches, centimeters, etc., and may be broken down or graduated into smaller units, e.g., eighths of inches, millimeters, etc. Alternatively, the strap scale may comprise a different scale or symbols, so long as it enables sizes to be recorded in a way that will provide accurate guidance in the selection and/or construction of garments for a particular individual, such as, for example, indicators for small, medium, large, extra large, or woman's sizes (e.g., 2, 4, 6, etc.). These are samplings of measurement indicia that may be used.

The strap scale 39 may comprise a measuring tape or other strip sewn into, embedded, or otherwise integrated or otherwise associated with the body of strap 32. The strap scale of measurement indicia measures distance from a reference starting point on the belt 22. The reference starting point on the belt 22 is an upper edge 22a of belt 22 opposite to the majority of strap 32. It should be understood that the second scale need not include continuous markings from the reference starting point. Although the upper edge 22a may serve as the reference starting point of the second scale, an optional gap or omission of measurement indicia can be provided adjacent the reference starting point. For example, in the event that the graduated measurement indicia are set forth in inches, the lowest marked indicia on strap 32 may be, for example, 4 inches representative of a distance of 4 inches from upper edge 22a.

Optionally the belt body and the strap body are made of a material simulating the appearance and texture of a material from which the garment is prepared or is to be prepared and/or the dimensions (height and thickness) of the waistband of the finished garment. This construction minimizes distortion of measurements and approximates the feel of the finished garment. For example, if measuring device 20 is to be used in measuring the fit of standard size jeans or in the preparation of tailoring a pair of jeans, the main bodies of belt 22 and strap 32 may be made of denim that simulates the dimensions, appearance and tactile feel of the waistband and crotch or outseam of the jeans, and may be made of identical denim as selected to make the jeans. Similarly, if measuring device 20 is to be used in selecting a standard stock size of a shirt or in tailoring a cotton shirt, the main bodies of belt 22 and strap 32 may be made of cotton. Thus, measuring device 20 may be made of various materials from which the garments are made or custom tailored. A user may be equipped with multiple measuring devices 20 having different dimensions and/or made of different materials from one another, in which case he or she will select the particular device 20 corresponding to the garment material.

Belt 22 is sufficient in length and flexibility to encircle the torso of most human adults. For example, belt 22 may be 3 to 8 feet in length. Strap 32 may have similar flexibility, and additionally is sufficient in length to measure the pants leg length or over shoulder torso dimension of an average human adult, if not a big and tall human adult. For example, strap 32 also may be 3 to 8 feet in length. The respective lengths of belt 22 and strap 32 may be the same or different from one another.

Other modifications and variations in addition to those described above may be made to the illustrated measuring device 20. By way of example, belt 22 may be modified to include a plurality of half-snaps or other fasteners along its length, wherein strap end 34 is capable of mating with belt 22 at any one of multiple positions along the length of the belt body. According to this embodiment, strap 32 is attachable to and detachable from multiple circumferential locations about encircled belt 22. According to a related modification, measuring device 20 comprises a plurality of straps for mating with the multiple half snaps or other fasteners on belt 22.

Measuring device 20 is suitable for use in measuring both the upper and lower body of a user to provide precise measurements to select an appropriate standard fit size for a particular garment and to produce most any custom-tailored garment without requiring use of any other devices or accessories. Measuring device 20 is particularly useful with respect to garment items such as pants, jeans, shorts, shirts, jackets, coats, skirts, blouses, dresses, hats and accessories.

Described below are methods for taking various measurements useful in selecting standard fit sizes and in tailoring custom-made lower body garments, such as pants, jeans, shorts, jackets and skirts. These methods are representative and not necessarily exhaustive of the manner in which the embodied measuring device 20 may be used for tailoring purposes.

Waist

The individual who is being measured (or the "measured individual" or end user) selects a material of which a pants garment is made or is to be prepared. A belt 24 may be selected that has a flexible belt body made of a material simulating the dimension, appearance and/or tactile feel of the waistband of the pants garment. The belt body may be substantially identical in width and thickness to the waistband and may be made of a material which is substantially identical to the material from which the waistband of the pants garment is made or is to be prepared. As a result, the present invention allows the user to approximate the feel of the actual waistband of the finished garment at the exact height that the individual desires to wear the waistband of the finished garment rather than providing a standard waist measurement of an individual that does not correspond to the desired ultimate waistband location of the finished garment.

Figure 6:
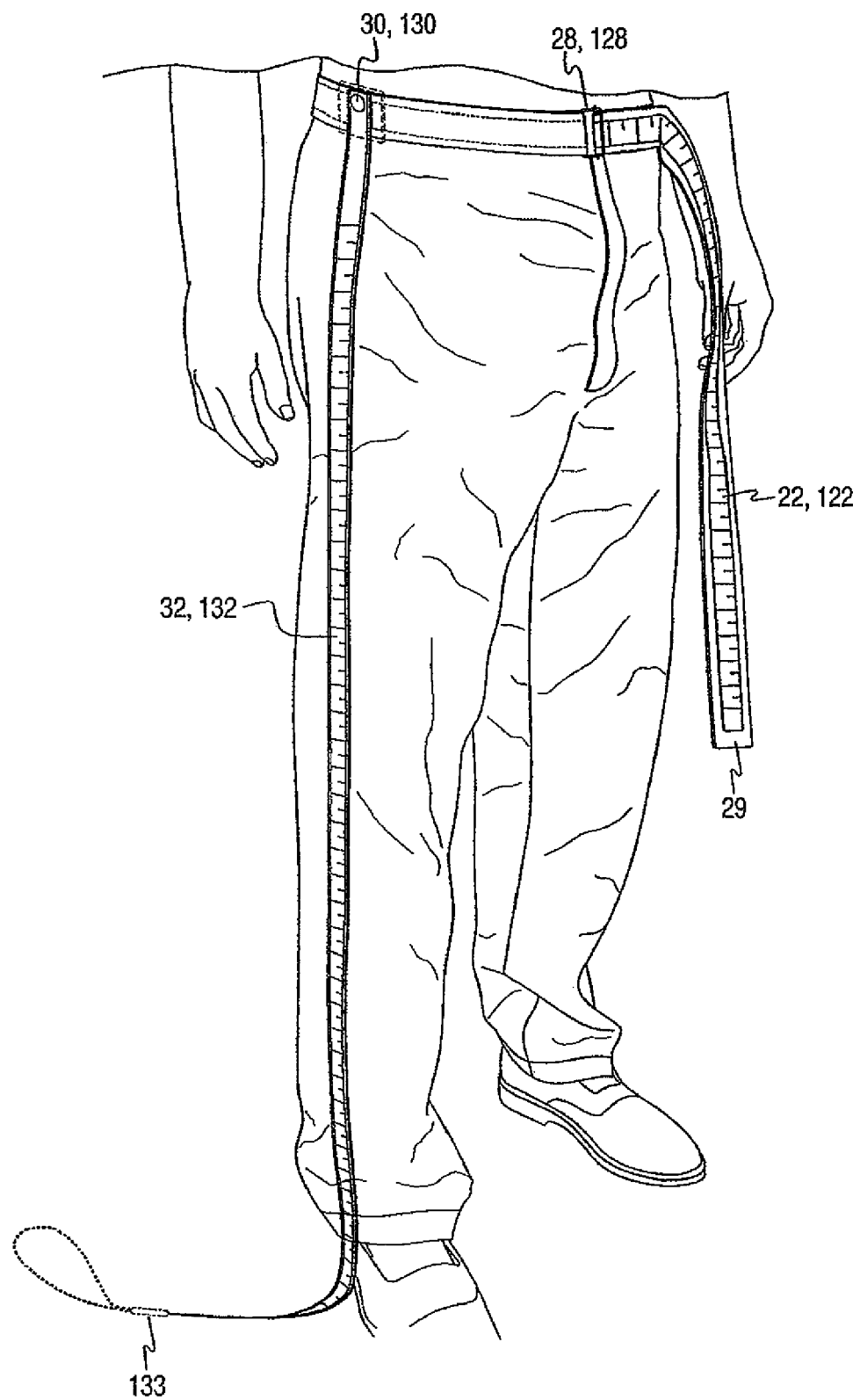
FIG. 6 is a depiction of the measuring device of FIG. 1 applied about the waist for taking waist and pants leg length measurements.

The individual will preferably obtain the measurements using the device when dressed in underwear or a similar form-fitting garment to improve the accuracy of the measurements. To begin, the belt 22 is encircled about the measured individual at the desired vertical location of the waistband of the finished garment, as shown in FIG. 6. Although this step may be performed by the tailor or the tailor's assistant, it is important to note that the measured individual may perform this task himself with equal success. This step likewise may be performed by trained personnel at a Fitness Center or by a Broker. The half snap of belt 22 positioned at upper edge 22a of belt 22 is arranged facing outward and, consequently, the belt face 24 is faced inward. A first segment of belt face 24 encircling the waist and situated inward is concealed from view, as are the measurement indicia present on the first segment of the belt face 24. The end 29 of belt 22 is first fed through buckle 28 and behind the locking bar 31, which is slidably attached to the buckle. The end 29 is then reversed in direction through the buckle 28 in front of the locking bar 31. The portion of belt 22 reversed through buckle 28 is designated herein as the second segment, and has its belt face 24 and corresponding measurement indicia located outward away from the waist due to the reversal in direction of belt 22. Consequently, the measurement indicia present on the second segment of first belt face 24 is exposed for viewing and recording. The buckle 28 and locking bar 31 provide infinite adjustment along the length of the belt 22. The vertical position of belt 22 is adjusted to occupy its proper position about the waist of the measured individual. Belt 22 is tightened or loosened to a desired comfort as instructed by the measured individual and/or as determined by the tailor, Fitness Center, or Broker.

The measured individual may adjust the height and tightness by himself or have another assist in locating belt 22 about his waist to match the intended location of the pants waistband with equal success. Since the buckle 28 secures the belt 22 once it is tightened, the belt remains stationary at the location selected by the individual because of the locking bar 31 of the belt buckle 28. As a result, the individual does not need to hold the belt in place either to obtain an accurate measurement or to judge the fit and feel of the waistband at the selected location. This feature further permits the individual to freely move with the belt to confirm that the location of the belt and tightness are going to be adequate and comfortable prior to recording the measurement.

A waist or circumferential measurement is then registered by reading the particular measurement indicia exposed (by reversing of belt 22) at buckle 28 and recording the measurement. The recording of this and other measurements described herein may comprise, for example, placing the measurement in written form, storing it in electronic form, such as on a computer or other electronic device, recording it orally on suitable media, such as a tape recorder, or any other recordation technique which permits the measurements to be recalled at a later time for selecting a standard size garment or for tailoring of the garment.

Strap 32 may be mated with or unmated with belt 22 (via fastener 30) during waist measurement. With strap 32 mated, strap 32 may be used to record a distance from the selected waist measurement location to reference point, such as the ground. The established nature of the reference point provides a fixed coordinate, from which any subsequent waist measurements may be made to improve the accuracy of repeat measurements, i.e., ensuring that all circumferential measurements for the waist are made at the same height or location.

Leg Length/Skirt Length

Fastener 30 is engaged to attach strap end 34 to belt 22, and belt 22 is encircled about the measured individual, as described above at the desired location of the waistband. The sequence of these two steps is not restricted. That is, belt 22 may be placed about the waist prior or subsequent to engaging strap end 34 and belt 22 with one another via fastener 30. Belt 22 is situated or rotated about the waist to place strap 32 at a circumferential position coinciding with the side of the leg, as shown in FIG. 6. Strap 32 is extended along the length of the side of the leg, and the measurement is registered. It is preferred that the measured individual place his shoes on prior to registering the measurement so that pants leg length may be registered accurately.

Since the belt 22 is located at and circles the measured individual at the desired location of the waistband of the individual, an extremely accurate measurement is obtained that precisely measures the outseam measurement of the individual from the location of the waistband in the garment rather than from the location of a standard tailor's waist measurement. Another factor contributing to the accuracy of the leg length measurement is the construction of the strap 32. As set forth above, the strap 32 may be constructed of the same material as the material of the garment or a simulation thereof. As a result, when obtaining the leg length measurement using the strap 32, the strap tends to drape in a way substantially similar to the outseam of the finished garment. It will be appreciated by one of skill in the art that the same technique as outlined above for obtaining the leg length can also be utilized to obtain the length of shorts or length of a skirt. In the case of a skirt, it may be further desired to obtain one or more additional measurements of the thigh of the individual using the belt 22 alone by circling one or both thighs at a predetermined location.

Overall Rise

Figure 7:
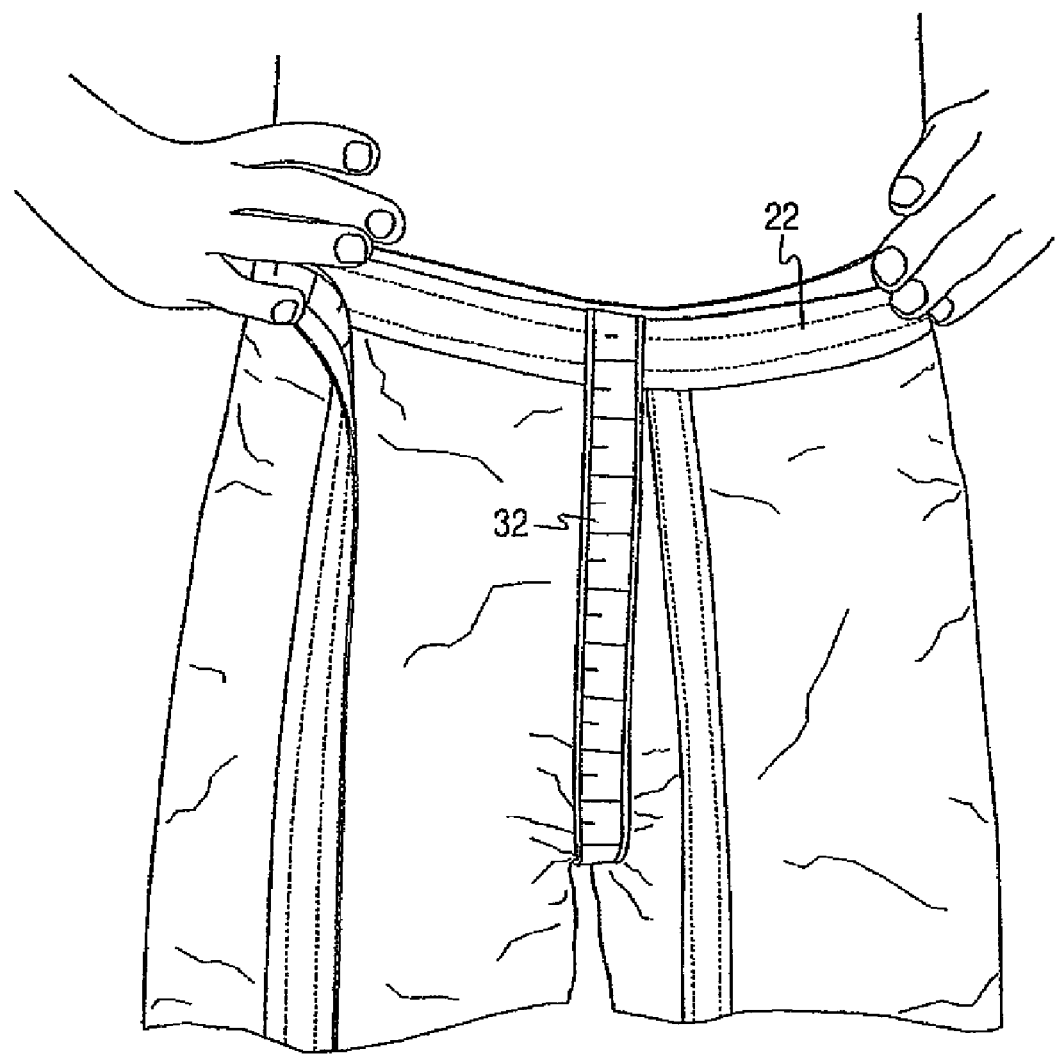
FIG. 7 is a depiction of the measuring device of FIG. 1 applied for taking an overall rise measurement.

As shown in FIG. 7, the overall rise is measured by placing belt 22 around the measured individual at the desired location of the waistband of the finished garment, as described above, and positioning fastener 30 at a circumferential position coinciding with the center of the back of the individual. In the event that overall rise is performed prior or subsequent to measuring pants leg length, belt 22 is simply rotated or revolved about the waist until fastener 30 is moved from the side of the leg to the center of the back, or vice versa.

Once belt 22 and strap 32 are properly positioned, strap 32 is pulled through the legs of the measured individual and raised to a circumferential position of belt 22 coinciding with the front center of the measured individual, as shown in FIG. 7. Overall rise is then registered as the measurement indicia of the scale 39 of strap 32 corresponding in location to upper edge 22a of belt 22.

Since strap 32 may be constructed of the same or substantially the same material as the finished garment and/or may have substantially the same dimensions of the crotch seam of that garment, accuracy of the overall rise measurement is enhanced. This is because the strap 32 as so constructed will approximate the feel and look of the ultimate crotch seam in the garment. Additionally regardless of the material used for the strap 32, the measurement of the overall rise is taken from the desired location selected by the individual of the waistband of finished garment rather than some standard or traditional location.

Rear Rise

With belt 22 and strap 32 situated as shown in FIG. 7 and described above for measuring overall rise, the end user or other person marks strap 32 at the lowest point of strap 32 through the crotch area. Marking may involve making a written notation on strap 32, or simply pinching strap 32. Fastener 30 is then disengaged to detach strap end 34 from belt 22, thereby permitting viewing of the marking, such as by removing strap 32 from between the end user's legs and raising the marking to eye level. The marking is then viewed and recorded for future use in selection of a stock fit size garment or preparation of the custom-tailored garment. These steps may be repeated to obtain multiple registrations and ensure accurate measurement.

Front Rise

Front rise may be calculated as the overall rise minus rear rise. Alternatively, front rise may be measured by rotating belt 22 about the waist to position fastener 30 at a circumferential position corresponding to the front center of the end user with the belt 22 at the desired location of the waistband of the finished garment. Strap 32 is then attached to belt 22 (if not already attached), fed through the legs of the end user, and passed upward to a circumferential position of belt 22 coinciding with the center rear of the measured end user. Strap 32 is pulled downward between the legs to create the desired rise elevation. Strap 32 is then marked at its lowest point, detached, and recorded similar to described above for measuring rear rise. It should be understood that measured overall rise and front rise may be used to calculate rear rise.

Strap 32 also may be used to record the distance between a reference point and the location about the waist that belt 22 is located for measuring the overall, front, and rear rises. The reference point may be, for example, the ground or belly button. The established nature of the reference point provides a fixed coordinate, from which any subsequent rise measurements may be made to improve the accuracy of repeat measurements, i.e., ensuring that all rise measurements are made at the same height or location.

The overall, front, and rear rise measurements may be taken without requiring removal of the strap 32 from the belt 22 or removal of the belt 22 from about the waist of the user. Maintaining the position of the belt 22 at its desired waistband location improves the accuracy of the rise measurements.

Buttocks/Thighs

The buttocks and thighs can be measured by encircling either strap 32 or belt 22, optionally detached from one another, around the widest part of the end user's buttocks and thighs, respectively.

It should be appreciated that the present invention permits all of the lower body measurements referred to above to be obtained using only the strap 32 and the belt 22 without a need for further devices or accessories. Additionally, all of these body measurements can be obtained without detaching the strap 32 from the belt 22.

With belt 22 secured around the buttocks or thigh, strap 32 may be used to record a distance from the selected measurement location to a reference point, such as the ground. The established nature of the reference point provides a fixed coordinate, from which any subsequent buttocks and thigh measurements may be referenced to improve the accuracy of repeat measurements, i.e., ensuring that all circumferential measurements for the buttocks and thigh are made at the same height or location on the user's body.

Described below are methods for taking various measurements useful in selecting appropriate stock sizes and tailoring custom-made upper body garments, such as jackets, dress shirts, T-shirts, hats, and accessories. These methods are representative and not necessarily exhaustive of the manners in which the embodied measuring device 20 may be used.

Chest/Bust and Lower Ribs

Either belt 22 or strap 32, optionally detached from one another, is encircled about the widest part of the chest of the measured individual, who preferably is in a standing position and holding in his or her breath. In the event that belt 22 is used, the graduated measurement indicia present on the first segment of belt 22 encircling the individual has face 24 directed inward and concealed from view. The end 29 of belt 22 is fed through buckle 28 and reversed in direction. The second segment of belt 22 fed through buckle 28 has the belt face 24 situated outward for viewing of measurement indicia present on the second segment of first belt face 24. Belt 22 is tightened or loosened to a comfortable fit for the individual. In this instance, the locking mechanism of the belt 22 may or may not be used. A chest circumferential measurement is registered by reading the particular measurement indicia exposed (by reversing of belt 22) at buckle 28 and recording the measurement. Since the belt 22 can be secured in position using the buckle 28, the individual does not need to hold the belt 22 in place and may move freely. This aids in confirming accurate placement of the belt and ensuring that the fit will be comfortable both while stationary and while moving.

Measurement of the torso in the lower rib area is then facilitated by sliding belt 22 or strap 32 downward to a height corresponding to the bottom of the rib cage, tightening belt 22 or strap 32 to a desired comfort, and registering a measurement, as described above. Alternatively, the lower rib torso area may be registered initially, and thereafter belt 22 is raised to measure the chest area.

With belt 22 secured around the chest, bust, or lower ribs, strap 32 may be used to record a distance from the selected measurement location to a reference point, such as the ground or the belly button. The established nature of the reference point provides a fixed coordinate, from which any subsequent buttocks and thigh measurements may be made to improve the accuracy of repeat measurements, i.e., ensuring that all circumferential measurements for the chest, bust, or lower ribs are made at the same height or location on the body.

Neck/Half-Shoulder/Half-Span

Figure 10:
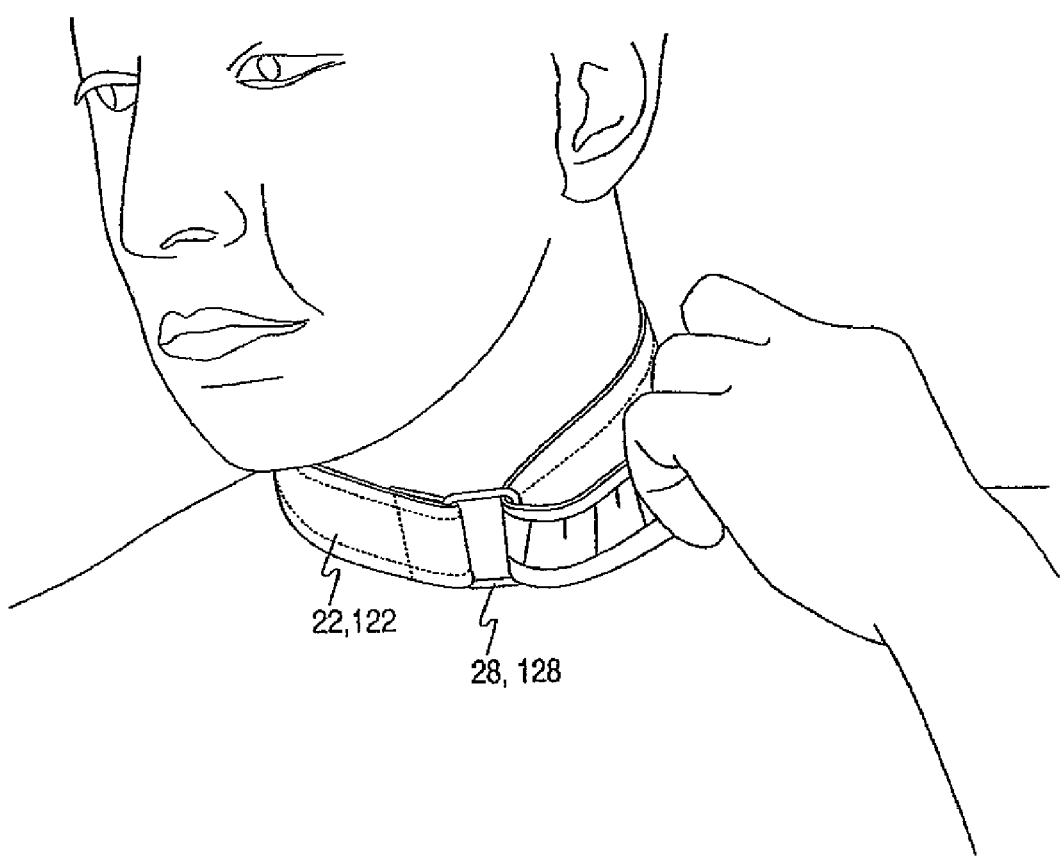
Figure 11:
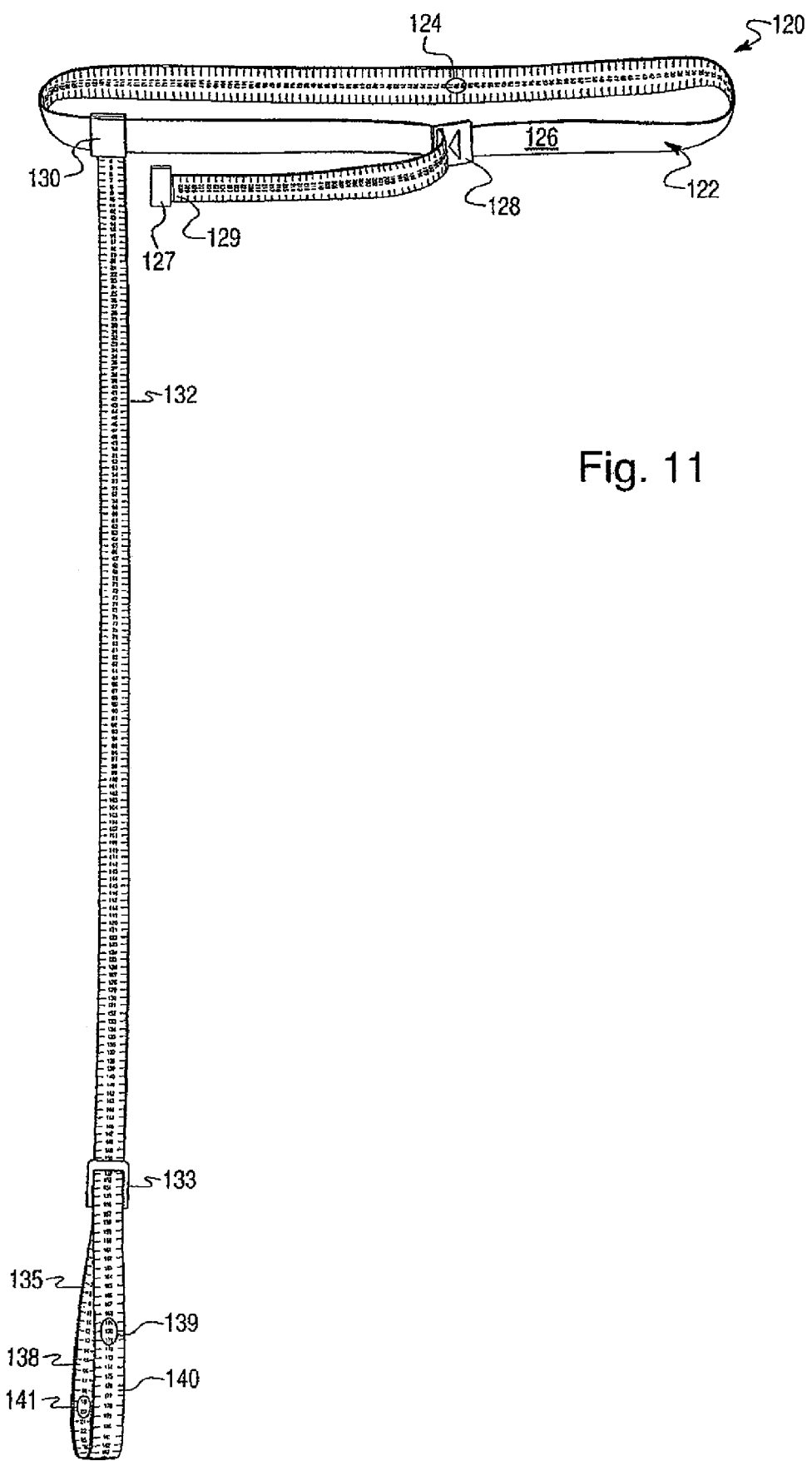
FIG. 11 is a top view of a measuring device according to another exemplary embodiment of the invention.

As illustrated in FIG. 10, in order to measure neck size for a shirt, jacket or other garment, belt 22 is encircled around the neck of the measured individual at the same location a collar of a shirt or other garment would be situated, and a circumferential measurement is registered from the scale 23. Preferably, the graduated measurement indicia present on the first segment of belt 22 encircling the individual has face 24 directed inward towards the neck and hidden from view (so that half-snap of fastener 30 on belt 22 faces outward). The end 29 of belt 22 is fed through buckle 28 and reversed in direction. The second segment of belt 22 fed through buckle 28 has the belt face 24 thereof situated outward for viewing of the scale of measurement indicia of belt face 24. Belt 22 is tightened or loosened to a comfortable fit for the individual, and neck size is registered by reading and recording the particular measurement indicia exposed at buckle 28. The buckle 28 secures the belt 22 in place without the need for additional support.

For measuring half-shoulder, fastener 30 is engaged to fixedly attach strap 32 along the length of belt 22, and belt 22 is encircled about the neck as described above. Attaching strap 32 to belt 22 in this manner prohibits the strap 32 from sliding along the length of the belt 22 while permitting full 360 degree rotation of the strap 32 in relation to the belt 22 about the point of the fastener 30. Fastener 30 may be engaged either prior or subsequent to encircling belt 22 about the neck. Belt 22 is rotated or revolved to position fastener 30 at a circumferential position corresponding to the vertebrae in the center rear of the neck. While retaining fastener 30 in place, strap 32 is extended along the slope of a first shoulder, and a first half-shoulder measurement is registered from the second scale since the strap 32 can be freely rotated about the fastener 30.

The device 20 can be used to accurately measure individuals of all different shoulder types (e.g., square shouldered or slope shouldered) from a fixed starting point without requiring removal or repositioning of the strap 32 from the belt 22. Another advantage provided by the rotatable strap 32 is that the risk of inaccurate measurement is eliminated due to inadvertent bending or folding of the strap to accommodate different shoulder structures.

Strap 32 is then rotationally pivoted about mated fastener 30 and extended along the slope of the opposite second shoulder, preferably while retaining the fastener 30 in place. Strap 32 is extended along the slope of the second shoulder, and the user registers a second half-shoulder measurement from the second scale of strap 32. Advantageously, the pivoting motion permitted by fastener 30 allows both shoulder spans to be measured from a common reference point without requiring removal and reattachment of the strap 32 to increase measurement accuracy. The rotatability of the strap 32 also permits accurate measurements even in the case where an individual might have a slightly different slope in opposing shoulders or a slightly asymmetrical upper back build.

Figure 9:
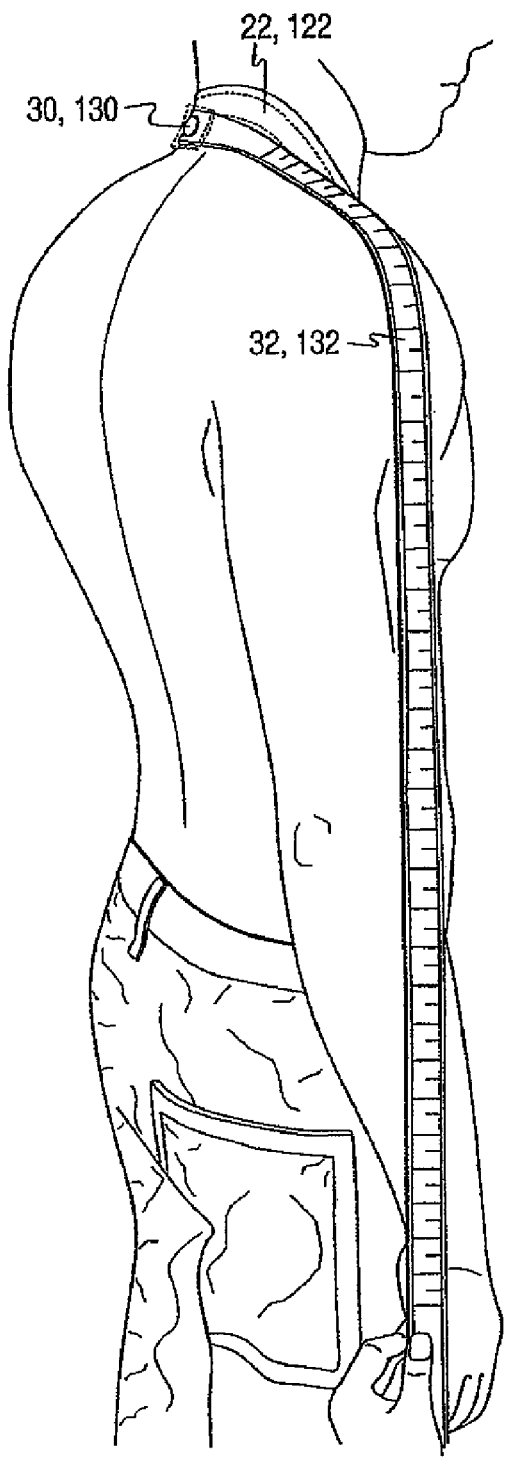
FIGS. 9 and 10 are depictions of the measuring device of FIG. 1 applied about the neck for taking upper body measurements.

The half-span is measured in substantially the same manner as half-shoulder, except that strap 32 is extended along extended arm to the hand, more preferably to the pinky knuckle, as shown in FIG. 9. All of the advantages set forth above with respect to the half shoulder measurement apply equally to the half span measurement as a result of the attachment of the strap 32 to the belt 22 in a manner that fixes it along the length of the belt while permitting full pivotal rotation of the strap 32. After registering a first half-span measurement, strap 32 is pivoted about fastener 30 as described above to register a second half-span measurement.

With belt 22 secured around the neck, strap 32 may be used to record a distance from the selected measurement location to a reference point, such as the ground. The established nature of the reference point provides a fixed coordinate from which any subsequent neck, half-shoulder, or half-span measurements may be made to improve the accuracy of repeat measurements, i.e., ensuring that subsequent are made at the same height or location on the neck.

Vertical/Head/Bicep/Wrist

The vertical measurement is taken by placing an end of either belt 22 or strap 32, optionally disengaged from one another, at the knot of the Adams apple and measuring to the center of the belly button. Head, bicep, and wrist measurements are taken by encircling either belt 22 or strap 32, optionally disengaged from one another, about the head, bicep, and wrist, respectively. With belt 22 secured around the head, bicep, or wrist, strap 32 may be used to record a distance from the selected measurement location to a reference point, such as the ground or belly button. The established nature of the reference point provides a fixed coordinate, from which any subsequent head, bicep, or wrist measurements may be made to improve the repeatability of measurements, i.e., ensuring that all circumferential measurements for the head, bicep, and wrist are made at the same height or location on the user's body.

Jacket

Figure 8:
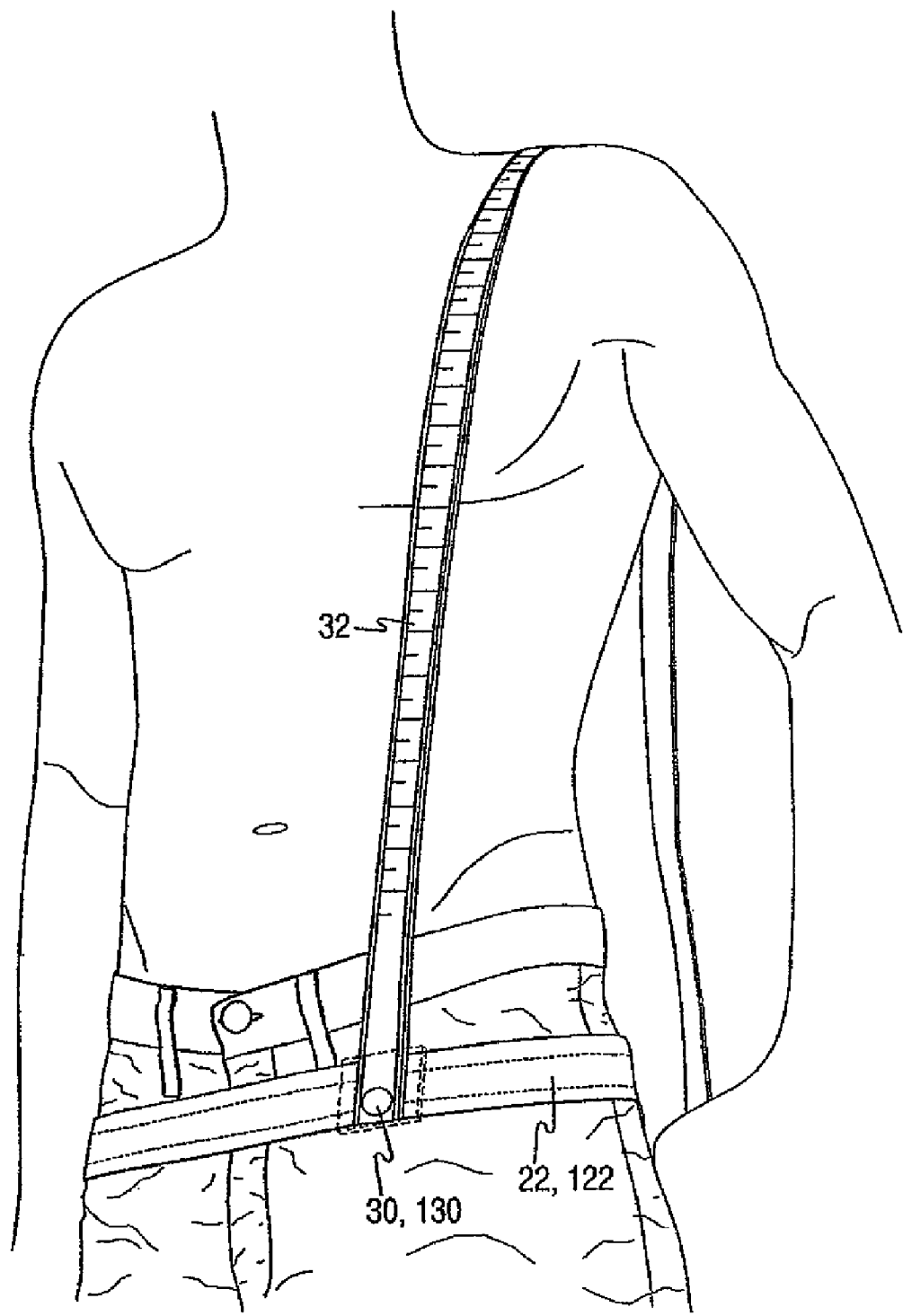
FIG. 8 is a depiction of the measuring device of FIG. 1 applied for taking a jacket measurement.

Turning to FIG. 8, belt 22 is encircled around the waist or hip area of the measured individual, and second end 29 of belt 22 is fed through buckle 28. Belt 22 is disposed at a height corresponding to the length of the jacket desired by the measured individual, so that edge 22a of belt 22 faces downward and coincides with the lower edge of the jacket. Fastener 30 is used to mate strap 32 with belt 22, either prior or subsequent to encircling of belt 22 about the individual's waist. While retaining belt 22 encircled about the waist or hips at the desired jacket length, strap 32 is extended up to and optionally over the shoulder of the individual. A jacket measurement is registered from the edge 22a to the point of the shoulder using the scale 39 of strap face 40. The jacket measurement can be used in selecting a standard size jacket or in preparing the custom-tailored jacket.

Utilizing the belt 22 to simulate the location of the bottom of a jacket yields several advantages. First, with the belt affixed to the individual, the individual is provided with both a visual and tactile representation of where the lower edge of the jacket will fall. The lower edge location may be selected by the individual based upon his or her particular preferences. Second, because the belt is affixed, the individual is permitted to move and turn in front of a mirror so as to judge whether the jacket length will be suitable both in the front and the back.

The use of the device 20 in measuring an individual for a jacket can also include taking additional measurements. For example, in addition to the measurement of the length and front panel of the jacket described above, the strap can be used in the configuration described and illustrated in FIG. 8 to obtain a back panel and overall panel measurement for the jacket. To more easily view the back panel and overall panel measurements, the orientation of the device 20 as shown in FIG. 8 may be altered to place the end of the strap 32 attached to the belt at the back side of the individual. As will be appreciated, if the fastener 30 is positioned at the back of the individual as opposed to the front as illustrated in FIG. 8, the individual being measured is more easily able to view the back and overall panel measurements without requiring assistance. The overall panel measurement is taken at the bottom front edge of the belt 22. The individual may calculate the back panel measurement by subtracting the front panel measurement from the overall panel measurement. The back panel measurement is particularly useful in obtaining a custom-fit jacket for individuals who are either large-busted or heavily muscled.

The measuring device 20 of the present invention can provide accurate measurements for virtually any article of standard fit size clothing and custom clothing by utilizing only a belt 22 and a strap 32 that are detachable from one another and reattachable to one another and permit rotational pivoting of the strap 32 in relation to the belt 22 at the point of the fastener 30.

Referring now more particularly to FIGS. 11 to 14, a measuring device according to another exemplary embodiment of the invention is generally designated by reference numeral 120.

Measuring device 120 comprises a belt 122 having a flexible belt body capable of being encircled about a body part of an individual, such as around a waist, neck, chest, arm, thigh, hip and/or head. The belt body has an inner face 124 and an opposite face 126 (See FIGS. 11 and 12). A buckle 128 is provided at one end of belt 122, and is sized to permit feeding of the opposite second end 129 of belt 122 through buckle or bracket 128. Attachment of buckle 128 to belt 122 may be accomplished in known manners, such as by folding over sewing excess belt length to create a loop securing buckle 128. In the exemplary embodiment, however, the buckle 128 is molded directly onto one end of belt by known injection molding techniques. As discussed in further detail below, belt 122 further comprises a molded end piece or blocking member 127 at the opposite second end 129. After the belt 122 is passed through the aperture 128' in the buckle 128, end piece 127 molded onto the end of the belt 122. The end piece 127 is larger than the aperture 128' so that the opposite second end 129 cannot pass back through the aperture 128'. Consequently, a continuous belt loop is established.

The inner face 124 has a first belt scale 123 of measurement indicia for providing circumference measurements. The first belt scale 123 may comprise a measuring tape, marking strip, etc. attached to, e.g., sewn into, the body of belt 122. Alternatively, the first scale may be embedded, integral with, marked on, or otherwise associated with the belt body. In the illustrated embodiment, the opposite face 126 of the belt body does not include a scale of measurement indicia but, instead, is provided with a logo, advertisement or other indicia. It should be understood, however, that it is within the scope of the invention to include a separate scale of measurement indicia on the face 126, and to make the scale of measurement indicia of the face 126 identical to or different from the indicia of the first scale on the inner face 124.

The first belt scale 123 is a unique measurement scale of consecutively numbered marks spaced by a quarter inch. Alternatively, the inner scale may comprise a different scale or symbols, such as, for example, indicators for small, medium, large, extra large, or women's sizes (e.g., 2, 4, 6, etc.). These are just examples of measurement indicia that may be used. The inner scale of measurement indicia employs the end of buckle 128 as a reference starting point for measuring distance along the belt 122.

Figure 12:
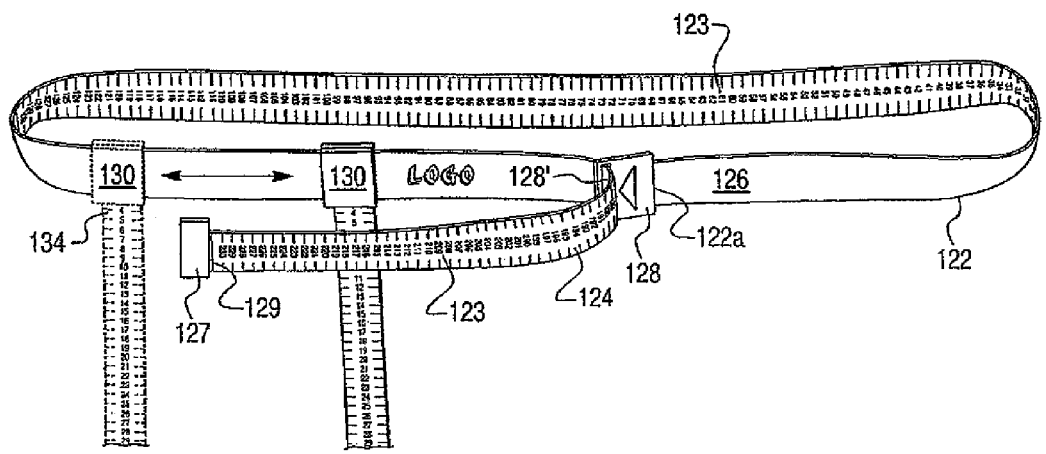
FIG. 12 is an enlargement of a portion of the view depicted in FIG. 11 showing the strap sliding relative to the belt via the fastener therebetween.
Figure 13:
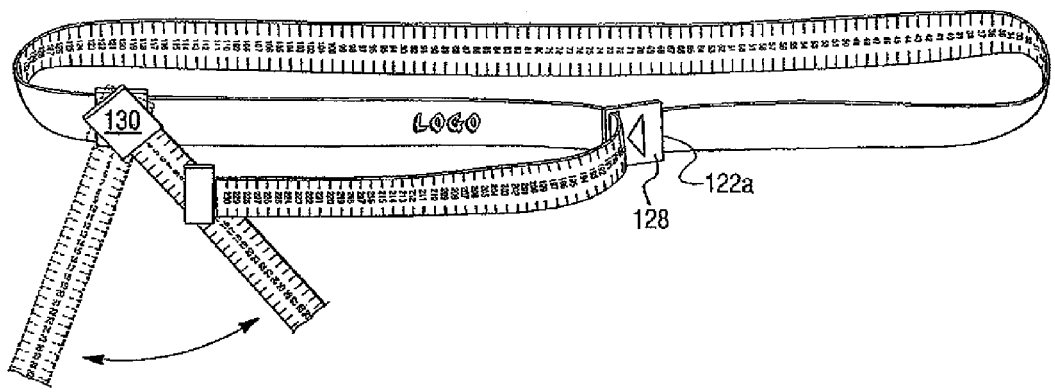
FIG. 13 is an enlargement of a portion of view of the measuring device of FIG. 11 showing the strap pivoting relative to the belt about the fastener therebetween.

Measuring device 120 further comprises a strap 132 having a strap end 134 secured to fastener 130, which is illustrated as a molded member. In an exemplary embodiment, the fastener 130 comprises a first component slidingly disposed on the belt body 122 to allow its longitudinal movement along belt, and a second component pivotally (rotatably) mounted on the first component. The first component of fastener 130 renders the attached strap end 134 slidable along the length of the belt 122. FIG. 12 illustrates the sliding capability of the strap 132 along the belt 122 with one (leftward) position shown in dotted line, and FIG. 13 illustrates the rotational capability of the strap 132 with respect to the belt 122. Because the axis of rotation of the fastener 130 is positioned at the centerline of the belt 122, the user achieves accurate measurements despite the rotational movement of the strap 132, i.e., from the same point on the centerline of the belt 122.

Accordingly, it should be understood that different types of relative movement between belt 122 and strap 132 are not necessarily restricted by fastener 130. For example, according to the exemplary embodiment fastener 130 provides a pivot point at the centerline of the belt 122 for permitting strap 132 to pivot rotationally about its point of attachment to the belt 122. See FIG. 13. The centering of the rotational axis of the fastener on the middle of the belt 122 provides more accurate measurement. It should be understood that other types of fasteners may be used in addition to or in place of the depicted fastener 130.

Fastener 130 optionally is repeatedly detachable from and re-attachable to belt 122, e.g., snap engagement of the first and second fastener components, without damage to belt 122 or strap 132 to permit detachment and re-attachment of fastener from belt 122. Fastener 130 provides additional advantages over prior known constructions. Prior constructions that attach a strap to a belt through a loop-type connection were prone to result in inaccurate measurements since, as the strap was tensioned, it would tend to bend or pull a section of the belt that was looped around out of alignment, for example, with the centerline of the belt. With the construction of the fastener 130 of the present invention, if undue tension is applied to the strap that might have a tendency to bend or move the belt 122 out of a true and accurate position or alignment, the fastener 130 can be designed to automatically uncouple the strap 132 from the belt 122 under a pre-selected amount of tension. Alternatively, fastener 130 may be permanently attached to belt 122.

Strap 132 has an inner face 138 and an opposite outer face 140. See FIG. 11. In the illustrated embodiment, in FIG. 11, outer face 140 features a second strap scale 139 of graduated measurement indicia. The attachment of strap end 134 to belt 122 as shown arranges the outer face 140, and hence the second strap scale 139, in an opposite direction (facing away) from the first scale 123 on inner face 124 of belt 122. In the illustrated embodiment, the inner face 138 of strap 132 includes a separate (third) scale 141 on the face 138. The third scale 141 is also a series of numbered marks spaced apart by a quarter inch; however, the numbered marks are in the opposite direction to the second strap scale 139 of outer face 140.

The second strap scale 139 is optionally the same as the belt scale 123. The strap scale may be a unique measurement scale of ¼ inches designated by consecutively numbered marks. Alternatively, the strap scale may comprise a different scale or symbols, as long as it enables sizes to be recorded in a way that will provide accurate guidance in the construction of garments for a particular individual, such as, for example, indicators for small, medium, large, extra large, or woman's sizes (e.g., 2, 4, 6, etc.). These are samplings of measurement indicia that may be used.

The second strap scale 139 may comprise a measuring tape or other strip sewn into, embedded, printed on, or otherwise integrated or otherwise associated with the body of strap 132. The strap scale of measurement indicia measures distance from a reference starting point on the belt 122. The reference starting point on the belt 122 may be, for example, an edge 122a of belt 122 or the centerline along the width of the belt 122. It should be understood that second scale need not include continuous markings from the reference starting point. An optional gap or omission of measurement indicia can be provided adjacent the reference starting point. For example, in the event that the graduated measurement indicia are set forth in quarter inches, the lowest marked indicia on strap 132 may be, for example, 4 representative of a distance of 1 inch from the reference point, e.g., upper edge 122a or the centerline of the belt width.

A third scale 141 measures distance from a reference starting point on the strap 132. The reference starting point for the third scale 141 is the opposite terminal end 135 of the strap 132. Notably, the strap 132 is provided with a clasp 133 at the terminal end 135 whereby the strap 132 is threaded through the clasp or loop bracket 133 to create a second continuous loop out of the strap 132. The formation of the second continuous loop in the strap 132 enhances the measurement capability of the overall device since the second continuous loop pervades a simplified structure to measure various body parts such as the calf, thigh, triceps, biceps, wrist, neck, head. etc. See for example FIG. 14. Therefore, the exemplary embodiment provides a unique dual loop structure where the belt 122 is formed as a first continuous (closed) loop with a first scale of measure 123 on at least one side and the strap 132 is also formed a second continuous (closed) loop having the second and third scales of measure 139, 141 on sides 138, 140, respectively.

Described below are methods for taking various measurements useful in selecting from standard or stock fit sizes and in tailoring custom-made lower body garments, such as pants, jeans, shorts, jackets and skirts with the measurement device 120 illustrated in FIGS. 11-14. These methods are representative and not necessarily exhaustive of the manner in which the embodied measuring device 120 may be used for tailoring purposes.

Waist

Figure 14:
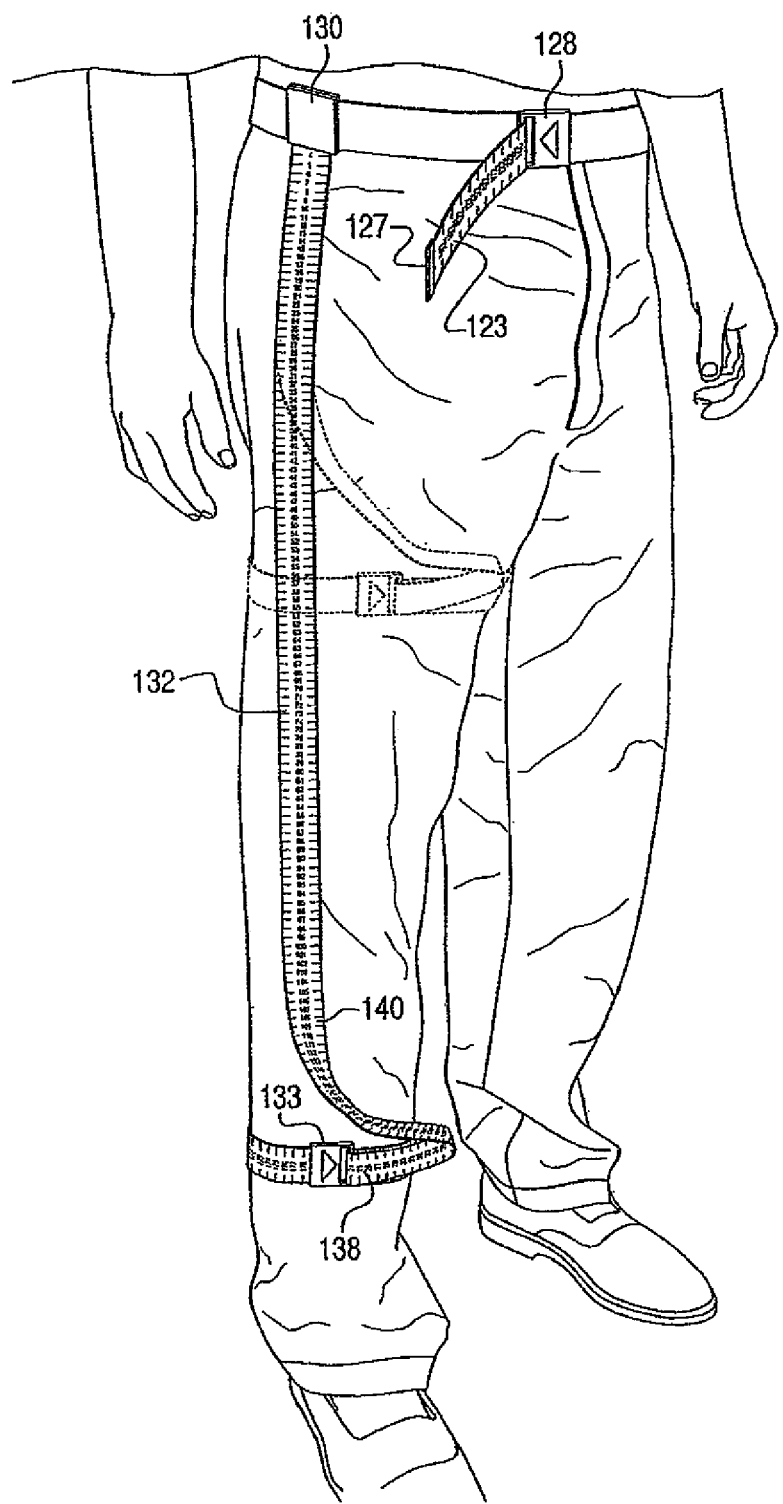
FIG. 14 is a depiction of the measuring device of FIG. 11 applied about the waist for taking waist, pants leg length measurements, calf measurement and thigh measurement.

The individual will preferably obtain the measurements using the device when dressed in underwear or a similar form-fitting garment to improve the accuracy of the measurements. To begin, the belt 122 is encircled about the measured individual at the desired vertical location of the waistband of the finished garment, as shown in FIGS. 6 and 14. Although this step may be performed by the tailor or the tailor's assistant, it is important to note that the measured individual may perform this task himself with equal success. This step likewise may be performed by trained personnel at a Fitness Center or by a Broker. The fastener 130 of belt 122 is arranged facing outward and, consequently, the belt face 124 is faced inward. A first segment of belt face 124 encircling the waist and situated inward is concealed from view, as are the measurement indicia present on the first segment of the belt face 124. The portion of belt 122 reversed through buckle 128 is designated herein as the second segment, and has its belt face 124 and corresponding measurement indicia located outward away from the waist due to the reversal in direction of belt 122. Consequently, the first scale 123 or measurement indicia present on the second segment of first belt face 124 is exposed for viewing and recording. The buckle 128 and molded end piece or blocking member 127 provides infinite adjustment along the length of the belt 122. The vertical position of belt 122 is adjusted to occupy its proper position about the waist of the measured individual. Belt 122 is tightened or loosened to a desired comfort as instructed by the measured individual and/or as determined by the tailor, Broker, or Fitness Center.

The measured individual may adjust the height and tightness by himself or have another assist in locating belt 122 about his waist to match the intended location of the pants waistband with equal success. A waist or circumferential measurement is then registered by reading the particular measurement indicia exposed (by reversing of belt 122) at buckle 128 and recording the measurement. The recording of this and other measurements described herein may comprise, for example, placing the measurement in written form, storing it in electronic form, such as on a computer or other electronic device, recording it orally on suitable media, such as a tape recorder, or any other recordation technique which permits the measurements to be recalled at a later time for selecting a standard size garment or for tailoring of the garment.

Strap 132 may be mated with or unmated with belt 122 (via fastener 130) during waist measurement. With strap 132 mated, strap 132 may be used to record a distance from the selected waist measurement location to reference point, such as the ground. The established nature of the reference point provides a fixed coordinate, from which any subsequent waist measurements may be referenced to improve the accuracy of repeat measurements, i.e., ensuring that all circumferential measurements for the waist are made at the same height or location on the wearer's body.

Leg Length/Skirt Length

Fastener 130 is engaged to attach strap end 134 to belt 122, and belt 122 is encircled about the measured individual, as described above at the desired location of the waistband. The sequence of these two steps is not restricted. That is, belt 122 may be placed about the waist prior or subsequent to engaging strap end 134 and belt 122 with one another via fastener 130. Belt 122 is situated or rotated about the waist or the fastener 130 is slid along the belt 122 to locate the strap 132 at a circumferential position coinciding with the side of the leg, as shown in FIGS. 6 and 14. Strap 132 is extended along the length of the side of the leg, and the measurement is registered. It is preferred that the measured individual place his shoes on prior to registering the measurement so that pants leg length may be registered accurately.

It will be appreciated by one of skill in the art that the same technique as outlined above for obtaining the leg length can also be utilized to obtain the length of shorts or length of a skirt. In the case of a skirt, it may be further desired to obtain one or more additional measurements of the thigh of the individual using the belt 122 alone by circling one or both thighs at a predetermined location.

Overall Rise

The overall rise is measured by placing belt 122 around the measured individual at the desired location of the waistband of the finished garment, as described above, and positioning fastener 130 at a circumferential position coinciding with the center of the back of the individual. FIG. 7 illustrates the positioning of belt 22 for measuring overall rise. In the event that overall rise is performed prior or subsequent to measuring pants leg length, belt 122 is simply rotated or revolved about the waist or the fastener 130 is slid along the belt 122 from the side of the leg to the center of the back, or vice versa.

Once belt 122 and strap 132 are properly positioned, strap 132 is pulled through the legs of the measured individual and raised to a circumferential position of belt 122 coinciding with the front center of the measured individual, as shown in FIG. 7. Overall rise is then registered as the measurement indicia of the second scale 139 of strap 132 corresponding in location to upper edge 122a of belt 122.

Rear Rise

With belt 122 and strap 132 situated as shown in FIG. 7 and described above for measuring overall rise, the individual or other person marks strap 132 at the lowest point of strap 132 through the crotch area. Marking may involve making a written notation on strap 132, or simply pinching strap 132. Fastener 130 is then disengaged to detach strap end 134 from belt 122, thereby permitting viewing of the marking, such as by removing strap 132 from between the individual's legs and raising the marking to eye level. The marking is then viewed and recorded for future use in selection of a standard size garment or in preparation of the custom-tailored garment. These steps may be repeated to obtain multiple registrations and ensure accurate measurement.

Front Rise

Front rise may be calculated as the overall rise minus rear rise. Alternatively, front rise may be measured by rotating belt 122 or sliding fastener 130 about the waist to position fastener 130 at a circumferential position corresponding to the front center of the individual with the belt 122 at the desired location of the waistband of the finished garment. Strap 132 is then attached to belt 122 (if not already or permanently attached), fed through the legs of the individual, and passed upward to a circumferential position of belt 122 coinciding with the center rear of the measured individual. Strap 132 is pulled downward between the legs to create the desired rise elevation. Strap 132 is then marked at its lowest point, detached, and recorded similar to described above for measuring rear rise. It should be understood that measured overall rise and front rise may be used to calculate rear rise.

Strap 132 also may be used to record the distance between a reference point and the location about the waist that belt 122 is located for measuring the overall, front, and rear rises. The reference point may be, for example, the ground or belly button. The established nature of the reference point provides a fixed coordinate, from which any subsequent rise measurements may be made to improve the accuracy of repeat measurements, i.e., ensuring that all rise measurements are made at the same height or location.

The overall, front, and rear rise measurements may be taken without requiring removal of the strap 132 from the belt 122 or repositioning of the belt 122 at the waistband. Maintaining the belt 122 at its desired waistband location improves the accuracy of the rise measurements.

Buttocks/Thighs

The buttocks and thighs can be measured by encircling either strap 132 or belt 122 around the widest part of the individual's buttocks and thighs, respectively.

It should be appreciated that the present invention permits all of the lower body measurements referred to above to be obtained using only the strap 132 and the belt 122 without a need for further devices or accessories. See FIG. 14. The second continuous loop of strap 132 and the two-sided scales of measure (scales 139, 141) provide the tools to measure both leg length via the second scale 139 and the calf diameter via the second loop and the third scale 141 as shown in FIG. 14. Additionally, all of these measurements can be obtained without detaching the strap 132 from the belt 122.

With belt 122 secured around the buttocks or thigh, strap 132 may be used to record a distance from the selected measurement location of the buttocks/thigh to a reference point, such as the ground. The established and constant nature of the reference point provides a fixed coordinate, from which any subsequent buttocks and thick measurements may be referenced to improve the repeatability of the measurements, i.e., ensuring that all circumferential measurements for the buttocks and thigh are made at the same height or location on the user's body.

Described below are methods for taking various measurements useful in selecting standard fit size and tailoring custom-made upper body garments, such as jackets, dress shirts, T-shirts, hats, and accessories. These methods are representative and not necessarily exhaustive of the manner in which the embodied measuring device 120 may be used.

Chest/Bust and Lower Ribs

Either belt 122 or strap 132 is encircled about the widest part of the chest of the measured individual, who preferably is in a standing position and holding in his or her breath. In the event that belt 122 is used, the graduated measurement indicia present on the first segment of belt 122 encircling the individual has face 124 directed inward and concealed from view. The second segment of belt 122 fed through buckle 128 has the belt face 124 situated outward for viewing of measurement indicia present on the second segment of first belt face 124. Belt 122 is tightened or loosened to a comfortable fit for the individual. In this instance, the locking mechanism of the belt 122 may or may not be used. A chest circumferential measurement is registered by reading the particular measurement indicia exposed (by reversing of belt 122) at buckle 128 and recording the measurement. Since the belt 122 can be secured in position using the buckle 128, the individual does not need to hold the belt 122 in place and may move freely. This aids in confirming accurate placement of the belt and ensuring that the fit will be comfortable both while stationary and while moving.

Measurement of the torso in the lower rib area is then facilitated by sliding belt 122 or strap 132 downward to a height corresponding to the bottom of the rib cage, tightening belt 122 or strap 132 to a desired comfort, and registering a measurement, as described above. Alternatively, the lower rib torso area may be registered initially, and thereafter belt 122 is raised to measure the chest area.

With belt 122 secured around the chest, bust, or lower ribs, the strap 132 may be used to record a distance from the selected measurement location to a reference point, such as the ground or the belly button. The established nature of the reference point provides a fixed coordinate from which any subsequent buttocks and thigh measurements may be referenced to improve repeatability. That is, by calibrating subsequent buttocks and thigh measurements using the strap 132 and measured distance to the reference point, the circumferential measurements are repeatedly made at the same height or location on the body.

Neck/Half-Shoulder/Half-Span

In the manner illustrated in FIG. 10, in order to measure neck size for a shirt, jacket or other garment, belt 122 or strap 132 is encircled around the neck of the measured individual at the same location a collar of a shirt or other garment would be situated, and a circumferential measurement is registered from the appropriate scale 123.

For measuring half-shoulder, fastener 130 is engaged to fixedly attach strap 132 along the length of belt 122, and belt 122 is encircled about the neck as described above. Fastener 130 may be engaged either prior or subsequent to encircling belt 122 about the neck. Fastener 130 is rotated or slid to position fastener 130 at a circumferential position corresponding to the vertebrae in the center rear of the neck. While retaining fastener 130 in place, strap 132 is extended along the slope of a first shoulder, and a first half-shoulder measurement is registered from the second scale since the strap 132 can be freely rotated about the fastener 130.

The device 120 can be used to accurately measure individuals of all different shoulder types (e.g., square shouldered or slope shouldered) from a fixed starting point without requiring removal or repositioning of the strap 132 from the belt 122. Another advantage provided by the rotatable and slidable strap 132 is that the risk of inaccurate measurement is eliminated due to inadvertent bending or folding of the strap to accommodate different shoulder structures.

Strap 132 is then rotationally pivoted about mated fastener 130 and extended along the slope of the opposite second shoulder, preferably while retaining the fastener 130 in place. Strap 132 is extended along the slope of the second shoulder, and the user registers a second half-shoulder measurement from the second scale of strap 132. Advantageously, the pivoting motion permitted by fastener 130 allows both shoulder spans to be measured from a common reference point without requiring removal and reattachment of the strap 132 to increase measurement accuracy. The rotatability of the strap 132 about fastener 130 also permits accurate measurements even in the case where an individual might have a slightly different slope in opposing shoulders or a slightly asymmetrical upper back build.

The half-span is measured in substantially the same manner as half-shoulder, except that strap 132 is extended along extended arm to the hand, more preferably to the pinky knuckle, in the manner shown in FIG. 9. All of the advantages set forth above with respect to the half shoulder measurement apply equally to the half span measurement as a result of the attachment of the strap 132 to the belt 122 in a manner that fixes it along the length of the belt while permitting full pivotal rotation of the strap 132. After registering a first half-span measurement, strap 132 is pivoted about fastener 130 as described above to register a second half-span measurement.

Vertical/Head/Bicep/Wrist

The vertical measurement is taken by placing an end of either belt 122 or strap 132 at the knot of the Adams apple and measuring to the center of the belly button. Head, bicep, and wrist measurements are taken by encircling either belt 122 or strap 132 about the head, bicep, and wrist, respectively. In an exemplary embodiment, belt 122 is encircled around the body part, and strap 132 is employed to measure a length distance to a common reference point, such as the ground or a point on the individual. With belt 122 secured around the head, bicep, or wrist, strap 132 may be used to record a distance from the selected measurement location to a reference point, such as the ground or belly button. The established nature of the reference point provides a fixed coordinate, from which any subsequent head, bicep, or wrist measurements may be referenced to improve the repeatability of measurements, i.e., ensuring that all circumferential measurements for the head, bicep, and wrist are made at the same height or location on the user's body part.

Jacket

In the manner shown in FIG. 8, belt 122 is encircled around the waist or hip area of the measured individual. Belt 122 is disposed at a height corresponding to the length of the jacket desired by the measured individual, so that edge 122a of belt 122 faces downward and coincides with the lower edge of the jacket. Fastener 130 is used to mate strap 132 with belt 122, either prior or subsequent to encircling of belt 122 about the individual's waist. As discussed above, fastener 130 optionally may permanently mate strap 132 with belt 122. While retaining belt 122 encircled about the waist or hips at the desired jacket length, strap 132 is extended up to and optionally over the shoulder of the individual. A jacket measurement is registered from the edge 122a to the point of the shoulder using the second scale 139 of strap face 140. The jacket measurement can be used in selection of a proper fit jacket or in preparation of the custom-tailored jacket.

Utilizing the belt 122 to simulate the location of the bottom of a jacket yields several advantages. First, with the belt affixed to the individual, the individual is provided with both a visual and tactile representation of where the lower edge of the jacket will fall. The location of the jacket lower edge can be selected by the individual based upon his or her particular preferences. Second, because the belt is affixed, the individual is permitted to move and turn in front of a mirror so as to judge whether the jacket length will be suitable both in the front and the back.

The use of the device 120 in measuring an individual for a custom-fit jacket can also include taking additional measurements. For example, in addition to the measurement of the length and front panel of the jacket described above, the strap can be used in the configuration described and illustrated in FIG. 8 to obtain a back panel and overall panel measurement for the jacket. To allow the individual being fitted to more easily view the back panel and overall panel measurements, the orientation of the device 120 as shown in FIG. 8 may be altered to locate the end of the strap 132 attached to the belt 122 at the back side of the individual. As will be appreciated, if the fastener 130 is positioned on the back of the individual as opposed to the front as illustrated in FIG. 8, the individual being measured may directly view the back and overall panel measurements without requiring the assistance of another. The overall panel measurement is observed at the bottom front edge of the belt 122. The individual may calculate the back panel measurement by subtracting the front panel measurement from the overall panel measurement. The back panel measurement is particularly useful in obtaining a custom-fit jacket for individuals who are either large-busted or heavily muscled.

A measuring device according to still another exemplary embodiment of the invention comprises continuous belt 122 of device 120 of FIGS. 11-14 without fastener 130 or strap 132.

The foregoing detailed description of the certain exemplary embodiments of the invention has been provided for the purpose of explaining the principles of the invention and its practical application, thereby enabling others skilled in the art to understand the invention for various embodiments and with various modifications as are suited to the particular use contemplated. This description is not intended to be exhaustive or to limit the invention to the precise embodiments disclosed. Modifications and equivalents will be apparent to practitioners skilled in this art and are encompassed within the spirit and scope of the appended claims.

What is claimed is:

1. A method of size fitting and processing garment orders, comprising:
    storing personal contact information and body measurements of multiple garment end users in a first database, the body measurements comprising first and second measurements obtained with a measurement device comprising a belt having a first scale of first measurement indicia and a strap having a second scale of second measurement indicia, the strap attached to the belt, the first measurement having been obtained from the belt placed at a first position on an individual garment end user and the second measurement having been obtained from the strap while the belt is maintained at the first position, at least the first measurement comprising a body measurement;
    storing garment pattern specifications of multiple garment items offered by a garment product provider in a second database, the garment pattern specifications ascertained from actual measurements of patterns of standard fit sizes of the garment items;
    receiving from a garment shopper an order for a garment item selected from the multiple garment items, and the personal contact information of an individual garment end user of the multiple garment end users for whom the selected garment item is to be purchased;
    comparing the body measurements of the individual garment end user, including at least the first measurement, to the pattern specifications of the standard fit sizes of the selected garment item; and
    automatically selecting for the garment shopper one of the standard fit sizes of the selected garment item based on the comparison.

2. The method of claim 1, further comprising:
    automatically placing an order of the selected standard fit size of the selected garment item for the garment shopper.

3. The method of claim 1, wherein the garment shopper and the garment end user are the same person.

4. The method of claim 1, wherein the first measurement comprises a circumferential body measurement and the second measurement comprises a distance to a fixed reference point.

5. The method of claim 1, wherein the first measurement comprises a circumferential measurement of a first body part and the second measurement comprises a length measurement of a second body part.

6. The method of claim 1, further comprising permitting the garment end users to access and update their respective body measurements in the first database.

7. The method of claim 1, wherein said storing of garment pattern specifications comprises storing in the second database respective garment pattern specifications of multiple garment items offered by a plurality of garment product providers.

8. The method of claim 1, wherein the first and second databases are the same.

9. The method of claim 1, wherein:
    said storing of personal contact information and body measurements further comprises storing personal fit preferences of the multiple garment end users; and
    said comparing comprises comparing the body measurements and the personal fit preferences of the individual garment end user with acceptable tolerances of the actual measurements of the standard fit sizes of the selected garment item.

10. The method of claim 1, wherein:
    the belt comprises a flexible belt body capable of being encircled about a body part of an individual, the belt body comprising first and second ends and opposite first and second belt faces, the first belt face comprising the first scale of the first measurement indicia for providing at least one member selected from the group consisting of length and circumference measurements;
    the strap comprises a flexible strap body with opposite first and second strap faces, at least one of the first and second faces comprising the second scale of the second measurement indicia for providing at least one member selected from the group consisting of length and circumference measurements; and
    the first end of the belt comprises a bracket with an aperture through which the belt body passes, the second end of the belt comprising a locking member having a size that is larger than the aperture such that the second end cannot pass through the aperture, whereby the belt is formed as a first closed loop.

11. The method of claim 1, wherein:
    the strap comprises a flexible strap body capable of being encircled about a body part of an individual, the strap body comprising first and second ends and opposite first and second strap faces, the first strap face comprising the second scale of the second measurement indicia for providing length measurements; and the first end of the strap comprises a bracket with an aperture through which the strap body passes, the second end comprising a locking member having a size that is larger than the aperture such that the second end cannot pass through the aperture, whereby the strap is formed as a closed loop.

12. A system comprising software and hardware for implementing a method of size fitting garments, the system configured to:

store personal contact information and body measurements of multiple garment end users in a first database, the body measurements comprising first and second measurements obtained with a measurement device comprising a belt having a first scale of first measurement indicia and a strap having a second scale of second measurement indicia, the strap attached to the belt, wherein the first measurement having been obtained from the belt placed at a first position on an individual garment end user and the second measurement having been obtained from the strap while the belt is maintained at the first position, at least the first measurement comprising a body measurement;

store garment pattern specifications of multiple garment items offered by a garment product provider in a second database, the garment pattern specifications ascertained from actual measurements of patterns of standard fit sizes of the garment items;

receive from a garment shopper an order for a garment item selected from the multiple garment items and the personal contact information of an individual garment end user of the multiple garment end users for whom the selected garment item is to be purchased;

compare the body measurements of the individual garment end user, including at least the first measurement, to the pattern specifications of the standard fit sizes of the selected garment item; and automatically select for the garment shopper one of the standard fit sizes of the selected garment item based on the comparison.

13. The system of claim 12, wherein the system is further configured to:

automatically place an order of the selected standard fit size of the selected garment item for the garment shopper.

14. The system of claim 12, wherein the system is further configured to permit the garment end users to access and update their respective body measurements in the first database.

15. The system of claim 12, wherein respective garment pattern specifications of multiple garment items offered by a plurality of garment product providers are stored in the second database.

16. The system of claim 12, wherein the first and second databases are the same.

17. The system of claim 12, wherein the system is further configured to:

store personal fit preferences of the multiple garment end users; and compare the body measurements and the personal fit preferences of the individual garment end user with acceptable tolerances of the actual measurements of the standard fit sizes of the selected garment item.

18. The system of claim 12, wherein:

the belt comprises a flexible belt body capable of being encircled about a body part of an individual, the belt body comprising first and second ends and opposite first and second belt faces, the first belt face comprising the first scale of the first measurement indicia for providing at least one of member selected from the group consisting of length and circumference measurements;

the strap comprises a flexible strap body with opposite first and second strap faces, at least one of the first and second faces comprising the second scale of the second measurement indicia for providing at least one of member selected from the group consisting of length and circumference measurements; and the first end of the belt comprises a bracket with an aperture through which the belt body passes, the second end of the belt comprising a locking member having a size that is larger than the aperture such that the second end cannot pass through the aperture, whereby the belt is formed as a first closed loop.

19. The system of claim 12, wherein:

the strap comprises a flexible strap body capable of being encircled about a body part of an individual, the strap body comprising first and second ends and opposite first and second strap faces, the first strap face comprising the second scale of the second measurement indicia for providing length measurements; and the first end of the strap comprises a bracket with an aperture through which the strap body passes, the second end comprising a locking member having a size that is larger than the aperture such that the second end cannot pass through the aperture, whereby the strap is formed as a closed loop.

20. A system for implementing a method of size fitting garments, the system comprising:

a first database storing personal contact information and body measurements of multiple garment end users in a first database, the body measurements comprising first and second measurements obtained with a measurement device comprising a belt having a first scale of first measurement indicia and a strap having a second scale of second measurement indicia, the strap attached to the belt, wherein the first measurement having been obtained from the belt placed at a first position on an individual garment end user and the second measurement having been obtained from the strap while the belt is maintained at the first position, at least the first measurement comprising a body measurement;

a second database storing garment pattern specifications of multiple garment items offered by a garment product provider in a second database, the garment pattern specifications ascertained from actual measurements of patterns of standard fit sizes of the garment items; and a server for receiving a garment shopper an order for a garment item selected from the multiple garment items and the personal contact information of an individual garment end user of the multiple garment end users for whom the selected garment item is to be purchased, comparing the body measurements of the individual garment end user, including at least the first measurement, to the pattern specifications of the standard fit sizes of the selected garment item, and automatically selecting for the garment shopper one of the standard fit sizes of the selected garment item based on the comparison.

21. A computer-readable medium containing instructions stored thereon which, when executed by a computer, cause the computer to perform a method of size fitting and processing garment orders, the method comprising:

storing personal contact information and body measurements of multiple garment end users in a first database, the body measurements comprising first and second measurements obtained with a measurement device comprising a belt having a first scale of first measurement indicia and a strap having a second scale of second measurement indicia, the strap attached to the belt, the first measurement having been obtained from the belt placed at a first position on an individual garment end user and the second measurement having been obtained from the strap while the belt is maintained at the first position, at least the first measurement comprising a body measurement;

storing garment pattern specifications of multiple garment items offered by a garment product provider in a second database, the garment pattern specifications ascertained from actual measurements of patterns of standard fit sizes of the garment items;

receiving from a garment shopper an order for a garment item selected from the multiple garment items, and the personal contact information of an individual garment end user of the multiple garment end users for whom the selected garment item is to be purchased;

comparing the body measurements of the individual garment end user, including at least the first measurement, to the pattern specifications of the standard fit sizes of the selected garment item; and automatically selecting for the garment shopper one of the standard fit sizes of the selected garment item based on the comparison.

22. The computer-readable medium of claim 21, wherein the computer-readable medium contains further instructions stored thereon which, when executed by the computer, cause the computer to:

automatically place an order of the selected standard fit size of the selected garment item for the garment shopper.

23. The computer-readable medium of claim 21, wherein the computer-readable medium contains further instructions stored thereon which, when executed by the computer, cause the computer to permit the garment end users to access and update their respective body measurements in the first database.

24. The computer-readable medium of claim 21, wherein respective garment pattern specifications of multiple garment items offered by a plurality of garment product providers are stored in the second database.

25. The computer-readable medium of claim 21, wherein the computer-readable medium contains further instructions stored thereon which, when executed by the computer, cause the computer to:

store personal fit preferences of the multiple garment end users; and compare the body measurements and the personal fit preferences of the individual garment end user with acceptable tolerances of the actual measurements of the standard fit sizes of the selected garment item.

26. The computer-readable medium of claim 21, wherein:

the belt comprises a flexible belt body capable of being encircled about a body part of an individual, the belt body comprising first and second ends and opposite first and second belt faces, the first belt face comprising the first scale of the first measurement indicia for providing at least one member selected from the group consisting of length and circumference measurements; and the strap comprises a flexible strap body with opposite first and second strap faces, at least one of the first and second faces comprising the second scale of the second measurement indicia for providing at least one member selected from the group consisting of length and circumference measurements, and the first end of the belt comprises a bracket with an aperture through which the belt body passes, the second end of the belt comprising a locking member having a size that is larger than the aperture such that the second end cannot pass through the aperture, whereby the belt is formed as a first closed loop.

27. The computer-readable medium of claim 21, wherein:

the strap comprises a flexible strap body capable of being encircled about a body part of an individual, the strap body comprising first and second ends and opposite first and second strap faces, the first strap face comprising the second scale of the second measurement indicia for providing length measurements; and the first end of the strap comprises a bracket with an aperture through which the strap body passes, the second end comprising a locking member having a size that is larger than the aperture such that the second end cannot pass through the aperture, whereby the strap is formed as a closed loop.

* * * * *